US008871817B2

(12) United States Patent
Türk et al.

(10) Patent No.: US 8,871,817 B2
(45) Date of Patent: Oct. 28, 2014

(54) POLYURETHANE THICKENERS

(75) Inventors: Holger Türk, Mannheim (DE); Volker Wendel, Seeheim-Jugenheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/278,700

(22) Filed: Oct. 21, 2011

(65) Prior Publication Data

US 2012/0101171 A1 Apr. 26, 2012

Related U.S. Application Data

(60) Provisional application No. 61/405,654, filed on Oct. 22, 2010.

(51) Int. Cl.
*C08G 18/87* (2006.01)
*A61Q 19/00* (2006.01)
*C08G 18/48* (2006.01)
*A61K 8/87* (2006.01)
*A61K 8/06* (2006.01)
*C08G 18/28* (2006.01)
*C08G 18/22* (2006.01)
*A61Q 9/04* (2006.01)
*A61Q 15/00* (2006.01)
*A61Q 19/04* (2006.01)
*A61Q 17/04* (2006.01)
*A61Q 5/12* (2006.01)
*A61Q 5/02* (2006.01)

(52) U.S. Cl.
CPC . *A61K 8/87* (2013.01); *A61Q 19/00* (2013.01); *A61Q 9/04* (2013.01); *A61Q 15/00* (2013.01); *C08G 18/4833* (2013.01); *A61Q 19/04* (2013.01); *A61K 8/06* (2013.01); *C08G 18/283* (2013.01); *C08G 2105/02* (2013.01); *A61Q 17/04* (2013.01); *A61Q 5/12* (2013.01); *C08G 18/222* (2013.01); *A61K 2800/10* (2013.01); *A61K 2800/548* (2013.01); *A61Q 5/02* (2013.01); *A61K 2800/48* (2013.01); *C08G 18/225* (2013.01)
USPC ................................. 514/772; 528/55; 528/57

(58) Field of Classification Search
CPC ........ A61K 8/06; A61K 2800/48; A61Q 5/02

USPC ...................................... 514/772.3; 528/55, 57
See application file for complete search history.

(56) References Cited

U.S. PATENT DOCUMENTS

| | | | |
|---|---|---|---|
| 4,079,028 A | 3/1978 | Emmons et al. | |
| 4,155,892 A * | 5/1979 | Emmons et al. | 524/507 |
| 4,704,446 A * | 11/1987 | Goel | 528/78 |
| 5,612,408 A | 3/1997 | Konig et al. | |
| 5,798,094 A * | 8/1998 | Vu et al. | 424/65 |
| 6,630,050 B1 * | 10/2003 | Moeller et al. | 156/331.7 |
| 6,642,302 B2 * | 11/2003 | Wamprecht et al. | 524/589 |
| 7,318,929 B2 | 1/2008 | Schieferstein et al. | |
| 2002/0183442 A1 | 12/2002 | Wamprecht et al. | |
| 2002/0188061 A1 | 12/2002 | Wamprecht et al. | |
| 2004/0028742 A1* | 2/2004 | Bigorra Llosas et al. | 424/486 |
| 2008/0108775 A1 | 5/2008 | Schieferstein et al. | |
| 2011/0064681 A1 | 3/2011 | Wendel et al. | |
| 2011/0166291 A1 | 7/2011 | Turk et al. | |
| 2012/0082629 A1 | 4/2012 | Turk et al. | |
| 2012/0101170 A1 | 4/2012 | Turk et al. | |

FOREIGN PATENT DOCUMENTS

| | | |
|---|---|---|
| EP | 0761780 | 3/1997 |
| EP | 1013264 | 6/2000 |
| EP | 1111014 | 6/2001 |
| EP | 1584331 | 10/2005 |
| WO | WO-02/088212 | 11/2002 |
| WO | WO-2006/002813 | 1/2006 |
| WO | WO-2009/135856 | 11/2009 |
| WO | WO-2009/135857 | 11/2009 |

OTHER PUBLICATIONS

L. Ladon; Titel: Concentration units (http://pages.towson.edu/ladon/concas.html, downloaded on Nov. 26, 2013), published 2001.*

* cited by examiner

*Primary Examiner* — Johann R Richter
*Assistant Examiner* — Yanzhi Zhang
(74) *Attorney, Agent, or Firm* — Servilla Whitney LLC

(57) ABSTRACT

The present invention relates to a single-stage process for preparing polyurethanes which comprise at least three hydrophilic sections, at least four hydrophobic sections, optionally allophanate segments and optionally isocyanurate segments, in the presence of alkali(ne earth) metal carboxylates or zinc carboxylates. Furthermore, the present invention relates to the polyurethanes themselves obtainable in this way, to the use thereof as thickeners for aqueous preparations, and to aqueous preparations comprising polyurethanes of this type.

7 Claims, 1 Drawing Sheet

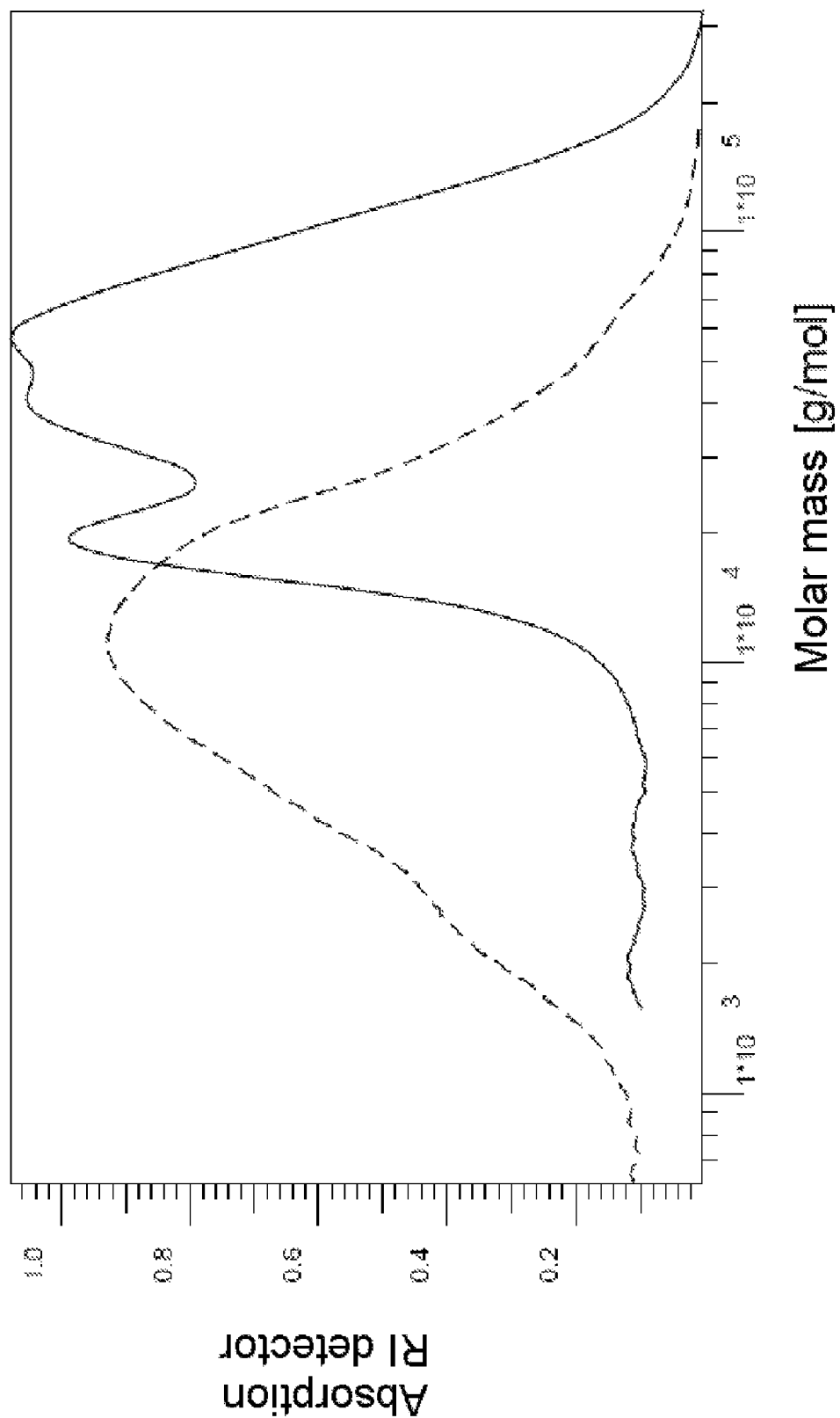

POLYURETHANE THICKENERS

CROSS-REFERENCE TO RELATED APPLICATIONS

This application claims priority under 35 U.S.C. §119(e) to U.S. Provisional Application No. 61/405,654, filed on Oct. 22, 2010, which is incorporated herein by reference in its entirety.

FIELD

Embodiments of the invention pertain to single stage processes for preparing polyurethanes, polyurethanes, their use of thickeners for aqueous preparations, and aqueous preparations containing polyurethanes.

BACKGROUND

Polyurethanes have been used for a long time in numerous fields of application for highly diverse purposes. Depending on the choice of starting materials and the stoichiometric ratio of the starting materials, polyurethanes are obtained with very different physicochemical properties.

Thickeners are used widely for increasing the viscosity of aqueous preparations, for example in the fields of cosmetics, human and animal nutrition, pharmacy and for detergents, paints and coatings. Inter alia, polyurethanes are also known as thickeners.

For example, polyurethane solutions or dispersions in water-dilutable aqueous or predominantly aqueous phase are referred to by the person skilled in the art as HEUR thickeners ("hydrophobically modified ethylene oxide urethane copolymer"), and have already been used for a relatively long time in highly diverse fields of application for thickening water-based emulsion paints.

The action principle of the thickening effect of the HEUR thickeners is assumed to be that the polyethylene glycol segments ensure the water compatibility and the hydrophobic segments construct a viscosity-imparting three-dimensional molecular association via an association with one another and also with dispersed binder particles of the emulsion paint to be thickened therein.

Thickeners are also used in the field of cosmetic preparations. Thickeners for cosmetic preparations are expected to have an adequate thickening effect even in preparations with a high content of salt. Furthermore, such thickeners should produce cosmetic preparations with a good texture and pleasant feel on the skin. Compatibility with numerous other auxiliaries, in particular with salts and surfactants, and also incorporability of the thickener itself and also of the other auxiliaries should be provided.

Moreover, the thickened preparations must have constant rheology and physical and chemical quality even upon long-term storage, and in the case of changes in temperature and pH. Finally, it should also be possible to produce these thickeners in a cost-effective manner and without a notable impact on the environment.

U.S. Pat. No. 4,079,028 and U.S. Pat. No. 4,155,892 disclose, inter alia, linear polyurethane thickeners. The preparation of the polyurethanes specified therein takes place in two stages in solution and is catalyzed by the catalyst dibutyltin dilaurate (DBTL) customary in polyurethane chemistry.

EP 1584331 and EP 1013264 describe polyurethane thickeners for cosmetic preparations. These are prepared in a single-step process from polyol, polyisocyanate and fatty alcohol, which may be ethoxylated, without use of a catalyst.

WO 2006/002813 describes polyurethane thickeners for various applications in aqueous media. These thickeners are prepared in a single-stage process from hydrophilic polyols having at least two hydroxy groups, one or more hydrophobic compounds, e.g. long-chain alcohols, and at least difunctional isocyanates. Here, an excess of NCO groups is used. The catalyst used is 1,8-diazabicyclo-[5-4-0]undec-7-ene (DABCO).

WO 02/88212 describes polyurethanes of ethoxylated long-chain alcohols and cyclic diisocyanate oligomers, for example isocyanurates. The polyurethanes described are prepared without using polyols and catalysts.

EP 725097 describes polyurethane thickeners, during the preparation of which a polyether mixture of polyetherols and alkoxylated monoalcohols are reacted with polyisocyanates in a single-stage with catalysis by DBTL, diazabicyclooctane or tin dioctoate, the ratio of NCO to OH equivalents being in the range from 0.9:1 to 1.2:1. These thickeners are proposed for use in the field of low shear forces, e.g. for the flow of water-based emulsion paints.

EP 1241198, EP 1241199, and EP 1241200 describe the preparation of polyurethane thickeners with DBTL catalysis and use of polyetherpolyols and urethane-group-containing polyetherpolyols with functionalities greater than 2, such as, for example, ethoxylated sugars or glycerol.

EP 761780 and EP 1111014 describe polyurethane thickeners of polyol, diisocyanate and branched alcohols. The preparation takes place in one stage without a diluent and without using catalysts.

WO 2009/135856 and WO 2009/135857 describe water-dispersible polyurethanes with an essentially linear backbone composed of alternating hydrophilic and hydrophobic sections and uses thereof. The polyurethane preparation takes place in two steps and is catalyzed by titanium or zinc compounds.

SUMMARY

Embodiments of the present invention relate to a single-stage process for preparing polyurethanes which comprise at least three hydrophilic sections, at least four hydrophobic sections, optionally allophanate segments and optionally isocyanurate segments, in the presence of alkali(ne earth) metal carboxylates or zinc carboxylates.

Further embodiments of the present invention relate to the polyurethanes themselves obtainable in this way, to the use thereof as thickeners for aqueous preparations, and to aqueous preparations comprising polyurethanes of this type.

BRIEF DESCRIPTION OF THE DRAWING

So that the manner in which the above recited features of the present invention can be understood in detail, a more particular description of the invention, briefly summarized above, may be had by reference to embodiments, some of which are illustrated in the appended figures. It is to be noted, however, that the appended figures illustrate only typical embodiments of this invention and are therefore not to be considered limiting of its scope, for the invention may admit to other equally effective embodiments.

FIG. 1 is a GPC chromatogram of polyurethanes obtained in accordance with one or more embodiments of the invention.

DETAILED DESCRIPTION

In accordance with various embodiments of the invention, provided are novel thickeners for water-comprising preparations, in particular cosmetic preparation. The preparation process should be easy and cost-effective to carry out and the novel thickeners should have the best thickening effect possible.

Moreover, the thickening effect of the novel thickeners should at least not be diminished by the presence of salts in the aqueous preparations.

It is also desired for the thickeners to have the lowest possible stickiness to surfaces such as glass or steel since this leads to advantages during the preparation of formulations. Thus, in the event of low stickiness, it is possible to achieve easier emptying of production vessels during the production of cosmetic preparations. Moreover, a good texture of the cosmetic preparations comprising the thickeners according to the invention is also important; in particular here, a smooth, nonlumpy or gritty structure is desired.

According to other embodiments of the invention, the polyurethane thickeners are tin-free, since this is desired for cosmetic applications.

Accordingly, one aspect of the invention relates to a process for preparing polyurethanes comprising
I) at least two hydrophilic sections S,
II) at least one hydrophilic section P different from S,
III) at least two terminal hydrophobic sections T,
IV) at least two hydrophobic sections D different from T,
where
a) to each section T is directly attached a section S,
b) to each section S on at least one side is attached at least one section D,
c) to each section P are attached at least two sections D,
where the preparation takes place in the presence of at least one carboxylic acid salt of at least one metal selected from the group consisting of the alkali metals, the alkaline earth metals, zinc and mixtures thereof, wherein the method is single-stage.

By means of the process according to one or more embodiments of the invention, polyurethanes are also obtained which comprise
I) at least two hydrophilic sections S,
II) no hydrophilic section P different from S,
III) at least two terminal hydrophobic sections T,
IV) a hydrophobic section D different from T,
where
a) to each section T is directly attached a section S and
b) to each section S is attached a section D.

The polyurethanes obtainable by the process according to the one or more embodiments of the invention are specifically dispersible in water. According to the invention, this comprises that they can also be emulsified in water or are completely or partially soluble in water.

The polyurethanes obtainable by the process according to one or more embodiments of the invention (also referred to herein below as "polyurethanes according to the invention") are specifically at least partially branched. "At least partially branched" means that at least some of the polymer molecules are not linear, but have branching points.

Such branches may be present both in the hydrophobic sections and also the hydrophilic sections.

In one embodiment of the invention, at least some of the terminal hydrophobic sections T are branched.

In one embodiment of the invention, at least some of the hydrophobic sections D are branched.

One advantage of the polyurethanes obtainable according to various embodiments of the invention is that by using alkali(ne earth) metal or zinc carboxylates it is possible to generate branches of the polyisocyanates in the form of isocyanurate or allophanate structures in-situ and it is therefore not necessary to rely on polyisocyanates with already prepared isocyanurate or allophanate structures as starting compounds. Firstly, the starting materials are more favorable in terms of cost as a result and secondly the desired amount of such branching points can be adjusted to the desired degree via the amount of catalyst. Furthermore, the process according to one or more embodiments of the invention leads less quickly to crosslinked structures than the use of prepared isocyanurate or allophanate structures.

The backbone of the polyurethanes according to one or more embodiments of the invention is composed of alternating hydrophobic and hydrophilic sections, where the hydrophobic and hydrophilic sections alternate in the sequence, but may be different in terms of their size, length and nature. In the polyurethanes according to a specific embodiment of the invention, a hydrophilic section is attached on both sides to a hydrophobic section. These hydrophobic sections may independently of one another be identical or different. Each section may be short-chain or an oligomer radical or a polymer radical. In the present case, "attached to a section" is understood as meaning that the connection takes place directly, i.e. that the two sections in question are directly adjacent in the polymer molecule.

Hydrophilic Sections

"Hydrophilic" is the term used here to refer to those sections which exhibit marked interaction with water. In general, hydrophilic sections consist of radicals of substances which are themselves hydrophilic.

Typical hydrophilic groups known to the person skilled in the art are, for example, nonionic polyether radicals. Polyether radicals may be homo-alkylene oxide radicals, or mixtures of different alkylene oxide radicals. These different alkylene oxide radicals may be present in the polyether radicals in random distribution or be present in block form. Specific polyether radicals are homo-ethylene oxide radicals. Herein below, ethylene oxide is also referred to as EO, and propylene oxide is also referred to as PO.

According to another embodiment, the polyether radicals comprise mixtures of EO radicals and PO radicals. These may be present in the polyether radicals in random distribution or be present in block form. In one specific embodiment, the EO and PO radicals are present in block form.

A particularly specific embodiment includes polyether radicals which have at least 50% by weight of ethylene oxide radicals, for example polyether radicals which have more than 50% by weight of ethylene oxide radicals, and propylene oxide radicals as further alkylene oxide radicals. The polyether radicals very particularly consist of ethylene oxide radicals.

The hydrophilicity of a substance can be determined, for example, by means of an opacity measurement of an aqueous solution.

According to specific embodiments, hydrophilic sections are water-soluble. For the purposes of this invention, a substance is referred to as being soluble in a liquid phase if at least 1 g, and in specific embodiments, at least 10 g, of the substance dissolved at 20° C. and a pressure of 1 bar to give a solution that looks clear to the human eye, i.e. without visible clouding in 1 liter of the liquid phase. Water-soluble substances are therefore substances which are soluble in an amount of at least 1 g, and in certain embodiments, at least 10 g, at 20° C. and a pressure of 1 bar to give a solution that looks clear to the human eye, i.e. without visible clouding, in 1 liter of water, and in specific embodiments, demineralized water.

Hydrophobic Sections

By means of the process according to one or more embodiments of the invention, polyurethane molecules are obtained which comprise in each case at least two terminal hydrophobic sections T and at least two further hydrophobic sections D.

By means of the process according to one or more embodiments of the invention, polyurethane molecules are also obtained which comprise at least two terminal hydrophobic sections T and only one hydrophobic section D.

In general, the hydrophobic sections consist of radicals of substances which are immiscible with water or only poorly miscible with water and are, in specific embodiments, lipophilic at the same time, i.e. are readily soluble in nonpolar solvents such as, for example, fats and oils.

Typical hydrophobic sections T are, for example, hydrocarbon radicals, in particular long-chain hydrocarbon radicals.

In one embodiment of the invention, the hydrocarbon radicals are unbranched. In another embodiment of the invention, the hydrocarbon radicals are branched.

In a further embodiment of the invention, the polyurethanes according to the invention comprise both branched and unbranched hydrocarbon radicals.

Long-chain aliphatic alcohols, aromatic alcohols and aliphatic diisocyanates are examples of hydrophobic substances, the radicals of which may be present in the hydrophobic sections of the polyurethanes according to the invention.

Polyurethanes prepared by the process according to one or more embodiments of the invention comprise at least two terminal hydrophobic sections (T) which, independently of one another, may be identical or different.

In one specific embodiment, at least some of the polyurethanes according to the invention comprise more than two terminal hydrophobic sections (T).

The terminal hydrophobic sections T can be branched or unbranched. Specifically, in certain embodiments, at least one of the two terminal hydrophobic sections T is branched.

In one specific embodiment, the terminal hydrophobic sections T comprise at least one alkyl radical. In one particularly specific embodiment, this alkyl radical comprises 4 to 30 carbon atoms, particularly 6 to 26 and very particularly 8 to 20 carbon atoms.

In another embodiment, this alkyl radical comprises 4 to 30 carbon atoms, particularly 8 to 30 and very particularly 12 to 30 carbon atoms.

According to certain specific embodiments, the chain length of the main chain of the alkyl radicals which are present in the sections T is 4 to 30 carbon atoms. These are for example radicals of linear or branched alkanes such as, for example, butane, isobutane, pentane, isopentane, neopentane, hexane, heptane, octane, 2-ethylhexane, nonane, decane, undecane, dodecane, tridecane, isotridecane, tetradecane, pentadecane, hexadecane, heptadecane, octadecane, nonadecane, icosane, henicosane, docosane, tricosane, isotricosane, tetracosane, pentacosane, hexacosane, heptacosane, octacosane, nonacosane, triacontane, 2-octyldodecane, 2-dodecylhexadecane, 2-tetradecyloctadecane, 2-decyltetradecane, or monomethyl-branched isooctadecane.

The hydrophobic sections T can likewise also comprise radicals of cycloalkanes and -alkenes, as described for example in EP 761780 A2, p. 4, ll. 56-58, radicals of alkenes as described for example in EP 761780 A2, p. 4, ll. 51-52, or alkylaryl radicals as described for example in EP 761780 A2, p. 4, ll. 53-55.

The sections T particularly may comprise the above-described alkyl radicals with a number of carbon atoms in the range from 8 to 30, very particularly may in the range from 12 to 30 carbon atoms.

The sections T, in certain embodiments, consist of aliphatic radicals, but may also comprise aromatic radicals.

In certain embodiments, at least one section T is a branched alkyl radical.

The side chains are may be also alkyl radicals or alkylene radicals, particularly may be alkyl radicals, in particular unbranched alkyl radicals.

In one embodiment, the side chains of the branched alkyl radicals have a chain length of at most 6, and in certain embodiments, of at most 4, carbon atoms.

In one embodiment, the branches are considerably shorter than the main chain. In one embodiment, each branch of the sections T of the polyurethanes according to the invention has a chain length which corresponds at most to half of the chain length of the main chain of this section T. In one embodiment, the branches are considerably shorter than the main chain. In one specific embodiment, the branched alkyl radicals are iso- and/or neo-alkyl radicals. In one specific embodiment, radicals of isoalkanes are used as branched alkyl radicals. In a specific embodiment the radical comprises a $C_{13}$-alkyl radical, in particular an iso-$C_{13}$-alkyl radical.

In another embodiment, the sections T comprise branched alkyl radicals, the side chains of which have a chain length of at least 4, and in a specific embodiment, of at least 6, carbon atoms.

The sections T can be introduced into the polyurethanes according to the invention in various ways.

In one specific embodiment, the sections T are introduced, simultaneously and together with hydrophilic sections S, through the use of alkoxylated alcohols.

Suitable alcohols are, for example, the alkoxylated linear alcohols from natural sources or from the Ziegler build-up reaction of ethylene in the presence of aluminum alkyl catalysts. Examples of suitable linear alcohols are linear $C_6$-$C_{30}$-alcohols, in particular $C_{12}$-$C_{30}$-alcohols. Particular alcohols which may be mentioned according to one or more embodiments are: n-dodecanol, n-tetradecanol, n-hexadecanol, n-octadecanol, n-eicosanol, n-docosanol, n-tetracosanol, n-hexacosanol, n-octacosanol and/or n-triacontanol, and also mixtures of the aforementioned alcohols, for example NAFOL® grades such as NAFOL® 22+ (Sasol).

oxoalcohols such as, for example, isoheptanol, isooctanol, isononanol, isodecanol, isoundecanol, isotridecanol (for example Exxal® grades 7, 8, 9, 10, 11, 13).

alcohols which are branched in the 2 position; these are the Guerbet alcohols known to the person skilled in the art which are accessible by dimerization of primary alcohols via the so-called Guerbet reaction. Particular alcohols which may be mentioned here are: Isofol®12 (Sasol), Rilanit® G16 (Cognis).

alcohols which are obtained by the Friedel-Crafts alkylation with oligomerized olefins and which then comprise an aromatic ring as well as a saturated hydrocarbon radical. Particular alcohols which may be mentioned here are: isooctylphenol and isononylphenol.

alcohols of the general formula (4) in EP 761780 A2, p. 4

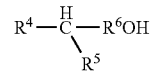

or alcohols of the general formula (5) in EP 761780 A2, p. 4

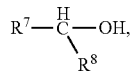

where
R$^4$, R$^5$, R$^7$ and R$^8$, independently of one another, have the meaning described in EP 761780 A2, p. 4, lines 45 to 58; and in certain specific embodiments, R$^4$, R$^5$, R$^7$ and R$^8$, independently of one another, are alkyl radicals having at least 4 carbon atoms and the total number of the carbon atoms in the alcohols is at most 30,
R$^6$ is an alkylene radical such as, for example, —CH$_2$—, —CH$_2$—CH$_2$—, —CH$_2$—CH(CH$_3$)—.

By way of example, mention may be made here of 2-decyl-1-tetradecanol as suitable alcohol.

In one embodiment, mixtures of ethoxylated C$_{16}$-C$_{18}$-fatty alcohols are used in order to introduce sections T into the polyurethanes.

In one embodiment, a linear, nonionic compound of the structural formula RO(CH$_2$CH$_2$O)$_x$H, where R is a linear C$_{16}$-C$_{18}$-alkyl radical, and where x=3, 5, 7, 8, 11, 13, 18, 25 or 80, and in certain specific embodiments, x=11, is used as at least one of the alcohols used. Commercially, such an ethoxylated, linear fatty alcohol is available, for example, as Lutensol® AT11.

In one embodiment of the invention, mixtures of ethoxylated linear and ethoxylated branched long-chain alcohols, in particular mixtures of the aforementioned types, are used.

In a further embodiment, ethoxylated iso-C$_{13}$-oxo alcohols or mixtures thereof are used in order to introduce sections T into the polyurethanes.

In one embodiment, a branched, nonionic compound of the structural formula RO(CH$_2$CH$_2$O)$_x$H, where R is a C$_{13}$-alkyl radical, and in certain specific embodiments, an iso-C$_{13}$-alkyl radical, and where x=3, 5, 6, 6.5, 7, 8, 10, 12, 15 or 20, and in certain specific embodiments, x=10, is used as at least one of the alcohols used. Commercially, such an ethoxylated, alkyl-branched alcohol is available, for example, as Lutensol® TO10.

In a further embodiment, mixtures comprising ethoxylated C$_{16}$-C$_{18}$-fatty alcohols and ethoxylated iso-C$_{13}$-oxo alcohols are used in order to introduce sections T into the polyurethanes.

In a further embodiment, the above-described alcohols of the general formula (4) or (5) in EP 761780 A2, p. 4, are used in their ethoxylated form in order to introduce sections T into the polyurethanes.

It is of course possible to additionally also introduce other sections T into the polyurethanes.

The hydrophobic sections T can of course also be introduced into the polyurethanes through any desired mixtures of the aforementioned ethoxylated alcohols.

By means of the process according to one or more embodiments of the invention, as is customary in the case of polymerization reactions, mixtures of different polymers are obtained, in the present case thus mixtures of different polyurethanes.

The term "polyurethane" used here can refer either to any individual polyurethane molecule or to the totality of the polyurethane molecules obtainable by the process according to one or more embodiments of the invention.

The polyurethanes obtainable according to the invention are, in certain specific embodiments, mixtures which comprise the described polyurethane structures.

Accordingly, the preparation of mixtures of polyurethanes, the terminal hydrophobic sections T of which are branched and/or unbranched alkyl radicals is also in accordance with the invention. The preparation of mixtures which comprise polyurethanes which comprise both branched and unbranched terminal, hydrophobic sections T is also in accordance with the invention.

At least some of the polyurethane molecules obtainable by the process according to one or more embodiments of the invention comprise allophanate segments.

The invention thus also provides a process according to one or more embodiments of the invention where at least some of the resulting polyurethanes comprise allophanate segments.

At least some of the polyurethane molecules obtainable by the process according to one or more embodiments of the invention comprise isocyanurate segments.

The invention thus also provides a process according to one or more embodiments of the invention where at least some of the polyurethanes comprise isocyanurate segments.

Hydrophilic Sections S

In the polyurethanes obtainable by the process according to one or more embodiments of the invention, to the terminal hydrophobic sections T are attached hydrophilic sections S.

In the polyurethanes, the sections S, independently of one another, may be identical or different.

The sections S, in certain embodiments, comprise radicals of alkylene oxides. In one specific embodiment, the number is in the range from 2 to 150 alkylene oxide radicals, and in a more specific embodiments, in the range from 2 to 100 alkylene oxide radicals, and in certain even more specific embodiments, in the range from 2 to 50 alkylene oxide radicals.

In certain embodiments, the hydrophilic sections S comprise or consist of ethylene oxide radicals. In one specific embodiment, the hydrophilic sections S comprise ethylene oxide radicals (EO units), the number of which is in the range from 2 to 150 EO units, and in a specific embodiment, in the range from 2 to 100 EO units and in an even more specific embodiment, in the range from 2 to 50 EO units.

In one specific embodiment, the sections S consist of 2 to 50, and in a specific embodiment, 2 to 25 EO units.

In another embodiment, the sections S consist of 25 to 100, and in a specific embodiment, 40 to 100 EO units.

The number of EO units per molecule of ethoxylated alcohol is also referred to as degree of ethoxylation.

The sections S can likewise comprise longer-chain alkylene oxide radicals, with the proviso that the sections S must be hydrophilic overall. The hydrophilicity can be controlled for example via the fraction of EO units in the sections S.

Hydrophobic Sections D

To each hydrophilic section S is attached at least one hydrophobic section D. Here, a section S may also be present in the interior of the molecule of the polyurethanes according to the invention. In this case, this section S is connected not like an edge-position section S directly to a section D and a section T, but on at least two sides to sections D. In a specific embodiment, a section S is connected in the interior of the molecule on both sides to one section D in each case.

For all edge-position sections S, it is the case that they are directly connected to an end-position section T.

Should a section S be branched to a low extent, then it can be directly connected at two or more positions to hydrophobic sections D. In a specific embodiment, to each hydrophilic section S is connected a hydrophobic section D on at least one side.

In a particularly specific embodiment, the sections S are unbranched and edge-positioned and connected directly to a terminal hydrophobic section T on one side and to a hydrophobic section D on the other side.

By means of the process according to one or more embodiments of the invention, polyurethane molecules are obtained which comprise at least two hydrophobic sections D. In addition, however, polyurethane molecules are also obtained which comprise only one hydrophobic section D.

In the polyurethane molecules with at least two hydrophobic sections D, these may be identical or, independently of one another, different.

The sections D can be branched with short-chain hydrophobic branches or be unbranched. In a specific embodiment, at least some of the sections D are branched.

In a specific embodiment, the sections D comprise at least one hydrophobic chain of carbon atoms, the length of which is in the range from 2 to 20 carbon atoms, and in a specific embodiment, 3 to 16 carbon atoms and in particular in the range from 4 to 12 carbon atoms.

In a specific embodiment, the sections D comprise diisocyanate radicals. The sections D particularly comprise radicals of aliphatic diisocyanates. Thus, for example, a hydrophobic section D can consist of one or more aliphatic diisocyanate radicals. In a specific embodiment, a section D consists of one to ten aliphatic diisocyanate radicals, particularly of one to five aliphatic diisocyanate radicals; very particularly, it comprises one, two or three aliphatic diisocyanate radicals.

The hydrophobic sections D can comprise aliphatic diisocyanate radicals with long, mid-length or short aliphatic units.

In one of the specific embodiments, the sections D of the polyurethanes prepared by the process according to one or more embodiments of the invention are cycloaliphatic or aliphatic diisocyanate radicals.

Aliphatic diisocyanate radicals are used as sections D in highly specific embodiments.

Aliphatic diisocyanates which may be mentioned by way of example are: 1,4-butylene diisocyanate, 1,12-dodecamethylene diisocyanate, 1,10-decamethylene diisocyanate, 2-butyl-2-ethylpentamethylene diisocyanate, 2,4,4- or 2,2,4-trimethylhexamethylene diisocyanate and in particular hexamethylene diisocyanate (HDI).

By way of example, cycloaliphatic diisocyanates which may be mentioned are: isophorone diisocyanate (IPDI), 2-isocyanatopropylcyclohexyl isocyanate, 4-methylcyclohexane 1,3-diisocyanate (H-TDI) and 1,3-bis(isocyanatomethyl)cyclohexane. So-called $H_{12}$-MDI or diisocyanates termed "saturated MDI", such as, for example, 4,4'-methylenebis(cyclohexyl isocyanate) (alternatively also called dicyclohexylmethane 4,4'-diisocyanate) or 2,4'-methylenebis(cyclohexyl)diisocyanate can also be present as radicals in sections D of the polyurethanes PU according to the invention.

It is of course possible, in the process according to one or more embodiments of the invention, to use mixtures of the abovementioned diisocyanates in order to prepare mixtures of different polyurethanes.

In one specific embodiment, some of the polyurethanes obtainable according to the invention comprise hydrophobic sections D with allophanate structures. Allophanate structures are formed as a result of the addition of an isocyanate group onto a urethane unit.

In one specific embodiment, polyurethanes prepared by the process according to one or more embodiments of the invention comprise hydrophobic sections D with isocyanurate structures. Isocyanurate structures are formed by the addition of 3 isocyanate groups (trimerization).

In a further specific embodiment, as a result of the process according to one or more embodiments of the invention, polyurethanes are obtained which comprise both hydrophobic sections D with allophanate structures and also hydrophobic sections D with isocyanurate structures.

In another embodiment, some of the polyurethanes prepared by the process according to one or more embodiments of the invention comprise hydrophobic sections D with biuret structures. Biuret structures are formed as a result of the addition of an isocyanate group onto a urea unit. Urea units in turn are formed as a result of the addition of primary amines onto isocyanate groups.

Hydrophilic Sections P

As a result of the process according to one or more embodiments of the invention, polyurethane molecules are obtained which comprise at least one hydrophilic section P different from the hydrophilic sections S. To a section P are directly attached at least two hydrophobic sections D. The sections P of the polyurethanes according to the invention can, independently of one another, be identical or different.

By the process according to one or more embodiments of the invention, polyurethanes are also additionally obtained which comprise no hydrophilic section P.

If more than one section P is present in a polyurethane according to the invention, then there is at least one hydrophobic section D between every two hydrophilic sections P.

If more than one section P is present in a polyurethane according to the invention, then these may be identical or different.

In one embodiment, polyurethanes obtainable according to the invention can comprise a sequence of sections in the order hydrophobic section D, then hydrophilic section S, then hydrophobic section D again between two hydrophilic sections P. Thus, if in a polyurethane according to the invention, more than one section P is present, then in such a case, the sections in the interior of the molecule can have a sequence of P-D-P or of P-D-S-D-P. Should more than two sections P be present, then both sequences in one molecule are possible.

In a specific embodiment, only one or two sections P are present in a molecule of the polyurethanes obtainable according to the invention.

The hydrophilic sections P are, in a specific embodiment, introduced into the polyurethanes through the use of hydrophilic polyols. Per molecule, these comprise at least two OH groups and at least two functional groups which are selected from the functions —O— (ether groups) and —COO— (ester groups), where the molecular weight of these hydrophilic compounds is at least 300, and in a specific embodiment, at least 1200.

One embodiment of the invention is a process according to one or more embodiments of the invention, wherein the at least one hydrophilic section P has a number-average molecular weight $M_n$ of from 1500 to 20 000 g/mol, and in a specific embodiment, from 4000 to 12 000 g/mol.

Suitable hydrophilic polyols are, for example, the polymerization products of ethylene oxide, the copolymerization or graft polymerization products thereof, and the polyethers obtained by condensation of polyhydric alcohols or mixture thereof and the polyethers obtained by ethoxylation of polyhydric alcohols, amides, polyamides and amino alcohols. Examples thereof are, for example, polyethylene glycols, addition products of ethylene oxide onto trimethylolpropane, EO-PO block copolymers, OH-terminated polyesters, such as, for example, those of the multifunctional polycaprolactone type.

In a specific embodiment, the hydrophilic polyols are polyetherpolyols. These are those hydrophilic polyols which comprise at least two OH groups and at least two —O— functions (ether groups) per molecule. These polyetherpolyols are generally so hydrophilic that they are water-soluble at room temperature (20° C.).

Of suitability for preparing the polyurethanes by the process according to one or more embodiments of the invention are those polyetherpolyols which comprise predominantly polyethylene glycol. In specific embodiments, if these polyethylene glycols have an average amount of EO units in the range from 30 to 450 per molecule.

In a specific embodiment, polyols of the general formula HO—$(CH_2—CH_2—O)_n$—H, where n can assume the values 30 to 450 are used. These are polyethylene glycols, which are condensation products of ethylene oxide with ethylene glycol or water.

In a specific embodiment, the molecular weight of these polyethylene glycols is adjusted to values in the range from 1500 to 20 000 g/mol, and in a specific embodiment, from 4000 to 12 000 g/mol.

However, it is also possible to use EO-PO block copolymers in order to incorporate the sections P into the polyurethanes obtainable according to the invention. For example, it is possible to use EO-PO block copolymers of the general formula HO-$(EO)_m$—$(PO)_n$-$(EO)_O$—H, where m and o, independently of one another, are integers in the range from 10 to 100, and in a specific embodiment, from 20 to 80, n is an integer in the range from 5 to 50, and in a specific embodiment, from 20 to 40, and where m, n and o are selected such that HO-$(EO)_m$—$(PO)_m$-$(EO)_O$—H is water-soluble.

According to the invention, the essentially linear polyether radicals which form the sections P and in a specific embodiment, have a number-average molecular weight $M_n$ of at least 1500 g/mol and at most 20 000 g/mol.

In one embodiment, these polyether radicals have number-average molecular weights $M_n$ in the range from 1500 g/mol to 15 000 g/mol.

In a further specific embodiment, these polyether radicals have number-average molecular weights $M_n$ in the range from 4000 g/mol to 12 000 g/mol.

In a particularly specific embodiment, these polyether radicals have number-average molecular weights $M_n$ in the range from 6000 g/mol to 12 000 g/mol.

The molecular weight $M_n$ of the sections P is particularly less than or equal to 10 000 g/mol and especially in the range from 6000 g/mol to 10 000 g/mol.

In a particularly specific embodiment, the linear polyether radicals have a number-average molecular weight $M_n$ of about 10 000 g/mol.

In a further particularly specific embodiment, the linear polyether radicals have a number-average molecular weight $M_n$ of about 6000 g/mol.

In a further particularly specific embodiment, the linear polyether radicals have a number-average molecular weight $M_n$ of about 9000 g/mol.

All of the hydrophilic sections S and P of the polyurethanes obtainable according to the invention may be polyether radicals.

In one specific embodiment, the hydrophilic sections of the polyurethanes according to the invention consist of
polyalkylene oxide units (sections P) and
polyethylene oxide units (sections S).

In one particularly specific embodiment of the polyurethanes obtainable by the process according to one or more embodiments of the invention, all of the sections P and S consist of EO units.

As a result of the process according to one or more embodiments of the invention, polyurethane molecules are obtained which comprise at least three hydrophilic sections. In one specific embodiment, these are two sections S and at least one section P.

Additionally, however, polyurethane molecules with only two hydrophilic sections S and without hydrophilic section P are also obtained.

As a result of the process according to one or more embodiments of the invention, polyurethanes are also obtained, according to embodiments the invention, which comprise I) at least two hydrophilic sections S,
II) no hydrophilic section P,
III) at least two terminal hydrophobic sections T,
IV) at least one hydrophobic section D different from T,
where
a) to each section T is directly attached a section S,
b) to each section S is attached a section D.

The polyurethanes prepared by the process according to one or more embodiments of the invention which additionally comprise allophanate structures comprise at least three sections S and specifically also at least one section P.

The polyurethanes prepared by the process according to one or more embodiments of the invention which additionally comprise isocyanurate structures comprise at least three sections S and also at least one section P.

At least some of the polyurethanes prepared by the process according to one or more embodiments of the invention are linear and have the following sequence of sections: T-S-D-P-D-S-T or T-S-D-P-D-P-D-S-T or T-S-D-S-T.

In one embodiment of the invention, at least some of the polyurethanes prepared by the process according to one or more embodiments of the invention comprise allophanate and/or isocyanurate structures and have the following sequence of sections:

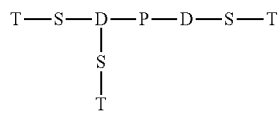

In one embodiment of the invention, at least some of the polyurethanes prepared by the process according to one or more embodiments of the invention comprise allophanate and/or isocyanurate structures and have the following sequence of sections:

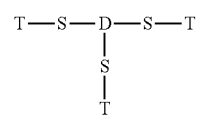

For example, polyurethanes prepared by the process according to one or more embodiments of the invention which additionally comprise allophanate structures have the following structure:

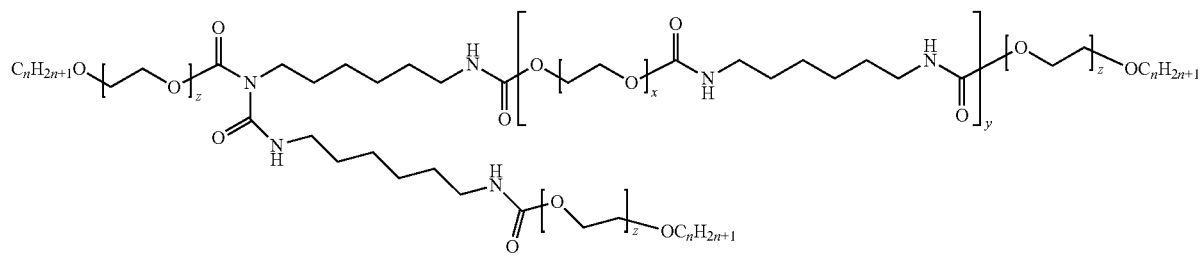

For example, polyurethanes prepared by the process according to one or more embodiments of the invention which additionally comprise isocyanurate structures have the following structure:

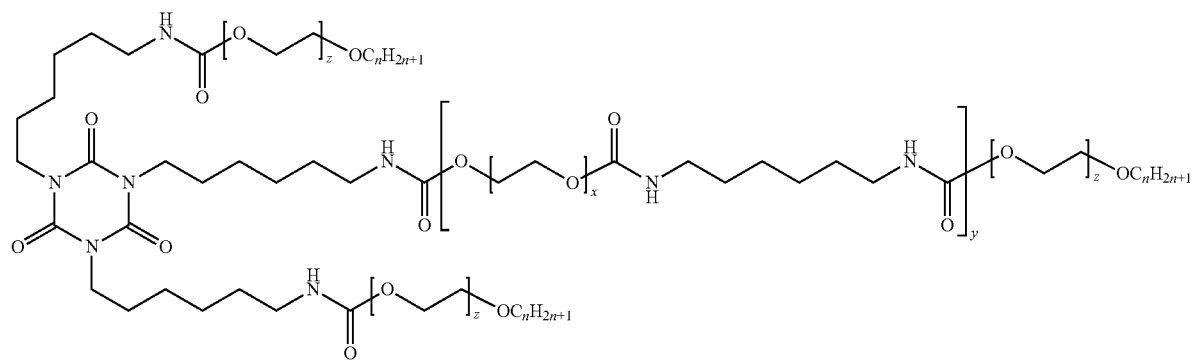

For each section P, it is the case that its molecular weight $M_n$ is greater than that of each section S present in the same molecule.

The ratio of the molecular weights $M_n$ of each hydrophilic section S of the polyurethanes according to the invention to the molecular weight $M_n$ of each hydrophilic section P is in the range from 1:1.4 to 1:140, and in a specific embodiment, in the range from 1:1.7 to 1:120.

In one specific embodiment, the ratio is 1:x, where x is equal to or greater than 2, and in a specific embodiment, equal to or greater than 2.3 and in an even more specific embodiment, specifically x is equal to or greater than 2.8.

The ratio can particularly be in the range from 1:2.8 to 1:115, very particularly in the range from 1:3 to 1:110 and especially in the range from 1:3.4 to 1:105.

In the process according to one or more embodiments of the invention, the ratio (mol to mol) of the polyols used to diisocyanates used can be in the range from 1:1.1 to 1:1.9. In a specific embodiment, the ratio is in the range from 1:1.1 to 1:1.8. The ratio may be particularly in the range from 1:1.1 to 1:1.75. The ratio may also especially in the range from 1:1.2 to 1:1.75. The ratio can of course also be 1:x where x is greater than or equal to 1.3, and in a specific embodiment, x is greater than or equal to 1.5.

In one embodiment, this results in no, one or two sections P being present in one molecule of the polyurethanes according to the invention.

In one embodiment, as a result of the process according to one or more embodiments of the invention, a mixture is obtained comprising polyurethanes without sections P, polyurethanes with one section P and polyurethanes with two sections P.

In one embodiment of the process according to one or more embodiments of the invention, in addition to the stated ranges of the ratio of polyetherdiols to diisocyanates, the ratio of polyetherdiols to ethoxylated alkanols is additionally chosen such that the molar quantitative ratio of polyetherdiols used to ethoxylated alkanols used is in the range from 5:1 to 1:2. In a specific embodiment, this ratio is in the range from 2:1 to 1:1.8, and in a specific embodiment, in the range from 1:1 to 1:1.6, and in an even more specific embodiment, specifically about 1:1.5.

In a particular embodiment of the invention, the molar quantitative ratio of polyetherdiols to diisocyanates to ethoxylated alkanols 1:1.75:1.5 is used.

As a result of the process according to one or more embodiments of the invention, mixtures of different polyurethanes are generally obtained. Such a mixture can comprise e.g. polyurethanes which have the same sequence of the sections T, S, D and/or P, but differ from one another structurally in at least one of the sections. One example of this which may be mentioned is a different section structure or a different section chain length. Thus, the sections T in a mixture of the polyurethanes prepared according to the invention can be different. For example, a mixture according to the invention can comprise polyurethanes, the sections T of which are all branched, and/or those, the sections T of which are all linear, and/or those polyurethanes which comprise both at least one linear section T and also at least one branched section T.

In one embodiment, the sum of the molecular weights of all sections T plus the molecular weights of sections D should be kept less than or equal to the sum of the molecular weights of all of the sections P.

Catalyst

To prepare the polyurethanes by the process according to one or more embodiments of the invention, the catalysts used are carboxylic acid salts of alkali metals, carboxylic acid salts of alkaline earth metals, carboxylic acid salts of zinc or mixtures thereof.

The carboxylic acids, the alkali(ne earth) metal salts or zinc salts thereof are used as catalysts in the process according to one or more embodiments of the invention are monocarboxylic acids of the general formula R—COOH, where R can be any desired organic, for example an aliphatic, an aromatic or a heterocyclic radical.

In a specific embodiment, R is an aliphatic radical, thus for example an alkyl radical, an alkenyl radical or an alkynyl radical. R can also comprise heteroatoms; for example, the carboxylic acid may be a hydroxycarboxylic acid.

In one embodiment of the invention, R is a hydrocarbon radical having 1 to 20, and in a specific embodiment, having 1 to 12, carbon atoms. R may be linear or branched, saturated or unsaturated.

In one embodiment of the invention, the carboxylic acid is acetic acid.

In a further embodiment of the invention, the carboxylic acid is octanoic acid.

In a further embodiment of the invention, the carboxylic acid is 2-ethylhexanoic acid.

In a further embodiment of the invention, the carboxylic acid is neodecanoic acid.

In a further embodiment of the invention, the carboxylic acid is n-decanoic acid.

In a further embodiment of the invention, the carboxylic acid is stearic acid.

In a further embodiment of the invention, the carboxylic acid is ricinoleic acid ((9Z,12R)-12-hydroxy-9-octadecenoic acid).

In a further embodiment of the invention, the carboxylic acid is a hydroxycarboxylic acid, such as, for example, citric acid or lactic acid, in particular lactic acid.

In a specific embodiment, if at least one carboxylic acid salt of an alkali metal is selected as catalyst, then the alkali metal is selected from sodium and potassium, particularly potassium.

If at least one carboxylic acid salt of an alkaline earth metal is selected as catalyst, then the alkaline earth metal is specifically selected from calcium and magnesium, particularly calcium.

A specific embodiment of the invention is the process wherein the preparation of the polyurethanes takes place in the presence of potassium carboxylate, and in an even more specific embodiment, potassium acetate.

Another specific embodiment of the invention is the process wherein the preparation of the polyurethanes takes place in the presence of potassium lactate.

A specific embodiment of the invention is the process wherein the preparation of the polyurethanes takes place in the presence of a zinc carboxylate, and in a specific embodiment, zinc neodecanoate.

It is of course also possible to use mixtures of two or more carboxylic acid salts of alkali(ne earth) metals or of zinc as catalysts for preparing polyurethanes PU according to the invention.

In one specific embodiment, a mixture comprising at least one potassium carboxylate and at least one zinc carboxylate is used. In a further specific embodiment, a mixture comprising potassium acetate and zinc neodecanoate is used. In another specific embodiment, a mixture comprising potassium lactate and zinc neodecanoate is used.

In addition to these catalysts, further catalysts known to the person skilled in the art in the field of polyurethane preparation can be used.

Such catalysts usually used in polyurethane chemistry are organic amines, in particular tertiary aliphatic, cycloaliphatic or aromatic amines, and Lewis-acidic organic metal compounds.

Suitable Lewis-acidic organic metal compounds are e.g. metal complexes such as acetylacetonates of iron, titanium, zinc, aluminum, cobalt, manganese, nickel and zirconium, such as e.g. zirconium 2,2,6,6-tetramethyl-3,5-heptanedionate. Further suitable metal compounds are described by Blank et al. in Progress in Organic Coatings, 1999, 35, 19 ff.

Bismuth, cobalt or zinc catalysts and also cesium or titanium salts can also be used as catalysts.

In one embodiment of the invention, the amount of such further catalysts which are not carboxylic acid salts of alkali metals, carboxylic acid salts of alkaline earth metals, carboxylic acid salts of zinc or mixtures thereof, is at most 10% by weight, and in a specific embodiment, at most 5% by weight, particularly at most 1% by weight and in particular at most 0.1% by weight, of the total amount of catalyst.

One embodiment of the invention is the process according to one or more embodiments of the invention wherein the preparation of the polyurethanes takes place in the presence of less than 10 ppm of tin, based on the reaction mixture.

In one embodiment of the invention, apart from the at least one carboxylic acid salt of a metal selected from alkali metals, alkaline earth metals, zinc and mixtures thereof, no further catalysts are used for preparing the polyurethanes.

In one specific embodiment, the catalyst or the mixture of catalysts is used in an amount in the range from 50 ppm to 5000 ppm, based on the total weight of all reacting compounds. In a specific embodiment, the catalyst is used in an amount in the range from 50 to 2500 ppm, particularly in an amount in the range from 100 to 1000 ppm, based on the total weight of all reacting compounds.

The catalyst can be added to the reaction mixture in solid or liquid form, depending on the nature of the catalyst. Suitable solvents are non-aqueous solvents such as, for example, aromatic or aliphatic hydrocarbons, inter alia toluene, xylene, ethyl acetate, hexane and cyclohexane, and also carboxylic acid esters, such as, for example, ethyl acetate. Further suitable solvents are acetone, THF, DMSO, DMF, DMAc and N-methylpyrrolidone and N-ethylpyrrolidone.

In a specific embodiment, the catalyst/catalyst mixture is used in dissolved form, and in an even more specific embodiment, particularly dissolved in the polyetherdiols with which the hydrophilic sections P are introduced into the polyurethanes.

The catalyst may already be present, at least partially, in the polyetherpolyols used for the process according to one or more embodiments of the invention if, during the preparation thereof, carboxylic acid salts of alkali(ne earth) metals have been used or have been formed.

In one embodiment of the invention, the polyetherpolyols used in the process according to one or more embodiments of the invention thus comprise at least some of the catalyst, if appropriate the total required amount of catalyst.

In one embodiment of the invention, the polyetherpolyols used in the process according to one or more embodiments of the invention prior to the start of the process already comprise at least some of the required catalyst and the remainder is added to carry out the process.

In the process according to one or more specific embodiments of the invention for preparing the polyurethanes, the following starting materials may be used:

A) Compounds which introduce the hydrophilic sections P into the polyurethanes: In specific embodiments, polyols of the general formula HO—$(CH_2$—$CH_2$—$O)_n$—H, where n assumes the values 30 to 450; these are polyethylene glycols which are condensation products of ethylene oxide with ethylene glycol or water. In a specific embodiment, the polyethylene glycols have a number-average molecular weight in the range from 6000 to 12 000 g/mol and in an even more specific embodiment, ones have a number-average molecular weight of from 6000 to 10 000 g/mol.

B) Compounds which introduce the terminal hydrophobic sections T and the hydrophilic sections S adjacent in each case to the sections T: in specific embodiments, ethoxylated $C_{16}$-$C_{18}$-fatty alcohols, ethoxylated iso-$C_{13}$-oxo alcohols, ethoxylated branched alcohols as in Production Examples 1 to 24 of EP 761780 A2 and mixtures thereof.

C) Compounds which introduce the hydrophobic sections D: aliphatic diisocyanates, in particular hexamethylene diisocyanate (HDI).

D) Catalysts: potassium carboxylate and/or zinc carboxylate.

The invention provides a process according to one or more embodiments of the invention, wherein, to prepare the polyurethanes, in each case at least one $C_4$-$C_{30}$-alcohol ethoxylated with 2 to 100 mol of ethylene oxide per mole, one polyetherdiol with a molecular weight $M_n$ in the range from 4000 to 12 000 g/mol and one diisocyanate are used.

The process according to one or more embodiments of the invention for the preparation of the polyurethanes comprises, in one embodiment, the following steps:

I) preparation of a mixture comprising
   a. at least one polyetherdiol with a molecular weight $M_n$ in the range from 1500 to 12 000 g/mol,
   b. at least one, optionally alkyl-branched $C_8$-$C_{30}$—, and in a specific embodiment, $C_{12}$-$C_{30}$-alkanol which has been ethoxylated with 2 to 150 mol, and in a further specific embodiment, with 2 to 100 mol, further and in a yet further specific embodiment, with 2 to 50 mol, in particular with 2 to 25 mol, of ethylene oxide per mol of alkanol,
   c. at least one carboxylic acid salt of at least one metal selected from alkali metals, alkaline earth metals or zinc, and in a specific embodiment, potassium carboxylate or zinc carboxylate,
II) optionally heating the mixture from step I) to 60 to 120° C., and in a specific embodiment, to 80 to 100° C.;
III) if appropriate, reducing the water content of the mixture, based on the total weight of the mixture, to at most 1000 ppm, and in a specific embodiment, at most 300 ppm,
IV) addition of at least one diisocyanate, and in a specific embodiment, hexamethylene diisocyanate, to the mixture;
V) leaving the resulting reaction mixture to react until the isocyanate content is at most 0.1% by weight, based on the total weight of the reaction mixture.

Reaction mixture is understood as meaning the totality of all substances which are present in the reaction space after the point at which the total amount of catalysts, isocyanates, substances reactive towards isocyanates and all further substances, such as for example solvents, have been completely supplied to the reaction space.

Solvents

Solvents is understood as meaning phases that are liquid at 20° C. and a pressure of 1 bar in which one or more of the starting materials for the polyurethanes, i.e. the substances which introduce the hydrophilic and/or hydrophobic sections into the polyurethanes or which act as catalyst, are soluble at 20° C. and 1 bar.

A specific embodiment of the invention is a process according to one or more embodiments of the invention wherein the amount of solvents, based on the reaction mixture, which are different from the substances which introduce the hydrophilic and hydrophobic sections into the polyurethanes or which act as catalyst is in the range from 0 to 10% by weight, and in a specific embodiment, from 0 to 5% by weight and in particular 0 to 1% by weight.

In one embodiment of the invention, the process according to one or more embodiments of the invention is carried out essentially in the absence of solvents which are different from the substances which introduce the hydrophilic and/or hydrophobic sections into the polyurethanes or which act as catalyst.

In one embodiment of the invention, the amount of substances which, following the complete addition of all substances during the reaction, are present in the reaction space and are neither catalysts, nor substances which are incorporated into the polyurethanes which form and consequently introduce the hydrophilic and hydrophobic sections into the polyurethanes, nor reaction products, is at most 10% by weight, and in a specific embodiment, at most 5% by weight, further specifically at most 1% by weight and particularly specifically at most 0.1% by weight, of the total amount of all of the substances present in the reaction space during the reaction.

In one specific embodiment, apart from the substances which introduce the hydrophilic and/or hydrophobic sections into the polyurethanes, the reaction products, if appropriate small amounts of water and catalyst, the reaction mixture comprises no further substances.

The specific process in which, apart from the starting materials for the polyurethane formation, no further solvents are used, leads to a more rapid reaction and solvents do not have to be separated off.

A further advantage of dispensing with solvents, in particular organic solvents which are different from the substances which introduce the hydrophilic and/or hydrophobic sections into the polyurethanes, is the better acceptance of the resulting polyurethanes as ingredients of cosmetic preparations.

If solvents are nevertheless used in the process according to one or more embodiments of the invention which are different from the starting materials for the polyurethane formation, then these are removed as far as possible after the reaction. "After the reaction" means the point at which the content of isocyanate groups is at most still 0.1% by weight, based on the total weight of the reaction mixture.

Single-Stage Process

The process according to one or more embodiments of the invention is single-stage. "Single-stage" means that the different substances with groups reactive towards isocyanate groups, thus for example the polyols and the ethoxylated alkanols, are essentially not brought into contact successively and separately, but simultaneously and together with the substances carrying isocyanate groups, for example the polyisocyanates.

One characteristic of the single-stage process is that all types of substances to be polymerized with groups reactive towards isocyanate groups are present alongside one another in the mixture at every point in the reaction.

However, it is not obligatory that the quantitative ratio of the different substances in this mixture is constant. Thus, for example, at certain points in the reaction, the amount of substances with two or more groups reactive towards isocyanate groups, based on the total amount of these substances to be incorporated by polymerization, may be greater than the amount of substances with one group reactive towards isocyanate groups that are to be polymerized, based on the total amount thereof. At other points, the quantitative ratios can be different therefrom.

One embodiment of the invention is the process according to one or more embodiments of the invention comprising the successive steps 1) preparation of a mixture comprising in each case at least some of the total amount of all of the substances with groups reactive towards isocyanate groups that are to be polymerized, 2) addition of at least some of the substances carrying isocyanate groups that are to be polymerized to the mixture prepared in step 1), 3) addition of those amounts of the substances to be polymerized which have not already been added in steps 1) and 2).

In the case of a two-stage reaction, firstly only the substances with two or more groups reactive towards isocyanate, i.e. for example the polyols, are brought into contact with an excess of polyisocyanate, giving prepolymers of the structure -D-P-D- and -D-P-D-P-D- with isocyanate chain ends, which are reacted in the second step with the substances with only one group reactive towards isocyanate groups, i.e. for example the ethoxylated monohydric alcohols, then giving the structures T-S-D-P-D-S-T or T-S-D-P-D-P-D-S-T. In the two-stage process, in the first stage, the majority of the substances with two or more groups reactive towards isocyanate is brought into contact with the substances carrying isocyanate groups, and the substances with only one group reactive towards isocyanate groups react in the second stage with the remaining isocyanate groups and form the chain ends of the polyurethanes.

In the case of the single-stage reaction, already from the start, in addition to the substances with two or more groups reactive towards isocyanate, for example the polyols, also at least some of the substances with only one group reactive towards isocyanate groups, for example the ethoxylated alkanols, are reacted with the substances carrying isocyanate groups. Consequently, in the one-stage reaction, from the start, as well as reaction products with the section sequences T-S-D-P-D-S-T and T-S-D-P-D-P-D-S-T, also those with the section sequence T-S-D-S-T are formed.

However, for the single-stage process, it is not obligatory that the entire amounts of all of the substances with groups reactive towards isocyanate groups that are to be polymerized are already provided at the start of the reaction. It is also possible that, at the start of the reaction, only in each case some of each substance with groups reactive towards isocyanate groups are provided in the reaction space and the remainder is added during the reaction.

In the single-stage process, the amount of polymers with the structure T-S-D-S-T is larger than in the two-stage process, whereas in the two-stage process the amount of polymers with the structure T-S-D-P-D-S-T is greater.

In one specific embodiment of the invention, the total amounts of all of the substances with groups reactive towards isocyanate that are to be polymerized are provided as a mixture and the substances carrying isocyanate groups are added to this mixture. In a specific embodiment, thus, for example the total amounts of polyols and alkoxylated alkanols are introduced as initial charge in the form of a mixture and the isocyanates are added to this mixture.

The mixture comprising the substances with groups reactive towards isocyanate that are to be polymerized specifically also comprises the catalyst or the catalysts and if appropriate solvents.

A specific embodiment of the invention is the process according to one or more embodiments of the invention comprising the successive steps 1) preparation of a mixture comprising the total amount of all of the substances with groups reactive towards isocyanate groups that are to be polymerized, 2) addition of the substances carrying isocyanate groups that are to be polymerized to the mixture prepared in step 1).

Such a single-stage process is also described for example in example 10 of EP 761780 A2 on p. 14, lines 29 to 47 and the following examples 11 to 24.

In a further embodiment of the invention, the total amount of these substances with two or more groups reactive towards isocyanate that are to be incorporated by polymerization and some of the substances with one group reactive towards isocyanate are introduced as initial charge in the form of a mixture and the total amount of the substances carrying isocyanate groups is added to this mixture. The remaining part amount of the substances with one group reactive towards isocyanate that are to be incorporated by polymerization is likewise added to the mixture following the addition of the substances carrying isocyanate groups.

In a further embodiment of the invention, in each case only some of the substances with two or more groups reactive towards isocyanate and some of the substances with one group reactive towards isocyanate are introduced as initial charge in the form of a mixture and the substances carrying isocyanate groups are added to this mixture. The remaining part amounts of the substances with two or more groups or one group reactive towards isocyanate that are to be incorporated by polymerization are likewise added to the mixture following the addition of the substances carrying isocyanate groups.

In one embodiment of the invention, the molar ratio of the groups reactive towards isocyanate:isocyanate groups following the addition of the total amount of substances carrying isocyanate groups is in the range from 0.7:1 to 1.3:1, and in a specific embodiment, from 0.8:1 to 1.2:1, particularly in the range from 0.9:1 to 1.1:1.

In one specific embodiment, the reaction products prepared by the process according to one or more embodiments of the invention are transferred to an aqueous phase. It is advantageous to separate off any solvents present prior to this transfer to the aqueous phase.

It is also advantageous to stabilize the aqueous mixture obtained after transferring the reaction products to water, for example by adding stabilizers (free-radical scavengers) and preservatives.

Suitable free-radical scavengers are for example hydroxy-TEMPO, 2,6-di-tert-butyl-p-kresol (Kerobit® TBK), hydroquinone monomethyl ether, tocopherol and mixtures of these compounds. These stabilizers are may be added in an amount of from 5 to 500 ppm, based on the weight of the aqueous mixture.

It is also advantageous to use preservatives. Of suitability are, for example, phenoxyethanol, methylisothiazolinone, ethylhexylglycerol, 3-acetyl-6-methyl-2H-pyran-2,4(3H)-dione, benzoic acid, parabens and mixtures of these substances. The preservatives are, in a specific embodiment, added in amounts of from 0.1 to 1% by weight, based on the aqueous mixture.

In a specific embodiment, the substances with groups reactive towards isocyanate groups that are used in the process according to one or more embodiments of the invention are essentially water-free in order to prevent a competing reaction of the isocyanate groups with water.

The water can advantageously be separated off from these substances by azeotropic distillation, drying in vacuo or other methods known to the person skilled in the art. For example, the water is removed up to a water content of the substances of at most 500 ppm, and in a specific embodiment, at most 300 ppm, based on the total weight of the substances.

The preparation of the actual reaction can for example involve exposing the substances with groups reactive towards isocyanate groups to reduced pressure, and in a specific embodiment, vacuum, and if appropriate elevated temperature, and thus largely removing the water.

The water-comprising substances can also be mixed with a solvent such as xylene, toluene or acetone and the water can be removed together with the added solvent by azeotropic distillation.

The invention further provides a process according to one or more embodiments of the invention wherein the substances with groups reactive towards isocyanate groups comprise at least in each case one alkoxylated $C_4$-$C_{30}$-alcohol, and in a specific embodiment, a branched $C_{12}$-$C_{30}$-alkanol, and at least in each case one polyetherdiol particularly a polyetherdiol with a molecular weight $M_n$ in the range from 4000 to 12 000 g/mol, and the substances carrying isocyanate groups comprise at least one diisocyanate, and in a specific embodiment, hexamethylene diisocyanate.

The invention also provides the use of the polyurethanes according to the invention for preparing aqueous preparations. Specific embodiments include preparations which comprise at least 5% by weight, in particular at least 20% by weight, very particularly at least 30% by weight and most particularly at least 50% by weight, of water. In specific embodiments, preparations may comprise at most 95% by weight, particularly at most 90% by weight and in particular at most 85% by weight, of water. The preparations comprising water are, for example, solutions, emulsions, suspensions or dispersions.

In addition to the polyurethanes obtainable by the process according to one or more embodiments of the invention, it is possible to use further substances for preparing the preparations, such as e.g. customary auxiliaries (for example dispersants and/or stabilizers), surfactants, preservatives, antifoams, fragrances, wetting agents, UV filters, pigments, emollients, active ingredients, further thickeners, dyes, softeners, humectants and/or other polymers.

The polyurethanes obtainable by the process according to one or more embodiments of the invention and mixtures thereof may be used for effectively and stably thickening preparations with a content of salts and pigments of more than 1% by weight, based on the preparation. Here, "stably" means maintaining an increased viscosity compared with the unthickened state over a period of several weeks and/or when increasing the temperature of the preparation, for example to up to 50° C.

The polyurethanes obtainable by the process according to one or more embodiments of the invention exhibit their thickening effect even at elevated temperatures up to about 50° C.

Furthermore, the polyurethanes obtainable by the process according to one or more embodiments of the invention exhibit a thickening effect in a broad pH from 2 to 13.

The polyurethanes obtainable by the process according to one or more embodiments of the invention furthermore have an influence on the structure of the preparations in which they enlarge the finely divided nature of the particles dispersed therein, i.e. reduce the particle size. Moreover, the polyurethanes obtainable by the process according to one or more embodiments of the invention permit the preparation of cosmetic preparations with good texture, i.e. particularly smooth, non-lumpy or gritty structures can be obtained.

On account of the reduced stickiness of the polyurethanes obtainable by the process according to one or more embodiments of the invention on surfaces such as glass or steel, the thickeners can be used particularly advantageously in standard commercial production vessels for producing cosmetic preparations.

The polyurethanes obtainable by the process according to one or more embodiments of the invention and mixtures thereof can also be used for preparing water-comprising preparations which comprise at least one salt or at least one surfactant or mixtures thereof.

In connection with the present invention, surfactants are also understood as meaning emulsifiers and also mixtures of surfactants and emulsifiers. In connection with the present invention, salt is understood as meaning salts and also salt-like structures also with a low $pK_a$ value and mixtures thereof.

The polyurethanes obtainable according to the invention are particularly used in order to prepare preparations which comprise at least 0.05% by weight of salt and/or at least 0.5% by weight of surfactants, very particularly comprising at least 0.1% (w/w) of salt and/or at least 1% by weight of surfactants.

In a further embodiment, the polyurethanes obtainable by the process according to one or more embodiments of the invention are used for preparing preparations which comprise at least 5% by weight, and in a specific embodiment, at least 10% by weight, of salt.

In a further embodiment, the polyurethanes obtainable by the process according to one or more embodiments of the invention are used for preparing preparations which comprise up to 25% by weight of surfactants, and in a further specific embodiment, up to 20% by weight and particularly 15% by weight or fewer surfactants.

In a further embodiment, the polyurethanes obtainable by the process according to one or more embodiments of the invention are used for preparing preparations which comprise at least 1% by weight of salt and up to 20% by weight of surfactants, s and in a specific embodiment, up to 15% by weight of surfactants.

The polyurethanes obtainable by the process according to one or more embodiments of the invention are used for preparing preparations which are oil-in-water emulsions.

Typically, oil-in-water emulsions comprise oil in the range from more than 0 to 40% by weight. In a specific embodiment, according to the invention, oil-in-water emulsions are prepared which comprise an oil fraction in the range from 5 to 40% by weight, particularly in the range from 10 to 35% by weight and in particular from 15 to 30% by weight, of oil.

The polyurethanes obtainable by the process according to one or more embodiments of the invention are very particularly used for preparing preparations which are oil-in-water emulsions and moreover comprise at least one salt.

The preparations according to the invention which comprise at least one polyurethane obtainable by the process according to one or more embodiments of the invention may be, for example, solutions, emulsions, suspensions or dispersions.

In one embodiment, a preparation according to the invention is a dispersion, and in a specific embodiment, an aqueous dispersion of the polyurethanes obtainable by the process according to one or more embodiments of the invention, as can be obtained from the reaction products by work-up after the preparation process. For this, for example, water is added to the reaction mixture after the reaction to produce a dispersion. If desired, the addition of a preservative and/or stabilizer can also take place.

In one embodiment, a dispersion according to the invention comprises up to 50% by weight of the polyurethanes obtainable according to the invention.

In another embodiment, a dispersion according to the invention comprises 25% by weight of the polyurethanes obtainable according to the invention.

In a specific embodiment, aqueous dispersions comprise up to 25% by weight of the polyurethanes obtainable according to the invention, at least one of the above-described preservatives suitable for cosmetic applications and, if desired, at least one of the above-described stabilizers (free-radical scavengers) suitable for cosmetic applications.

In another embodiment, the polyurethane obtainable according to the invention is in the form of a powder. Such a powder can be obtained, for example, by spray-drying or freeze-drying the aqueous dispersion.

To prepare the preparations according to the invention, which may be, for example, solutions, emulsions, suspensions or dispersions, the polyurethanes according to the invention may be used in the form of aqueous dispersions or as a powder, as can be obtained, for example, from the preparation process by appropriate work-up.

Further ingredients may be present in the preparations according to the invention depending on the intended use.

The preparations comprising the polyurethanes according to the invention can comprise further thickeners. Such further thickeners are known to the person skilled in the art. Suitable thickeners are specified for example in "Kosmetik and Hygiene von Kopf bis Fuβ [Cosmetics and Hygiene from Head to Toe]", Ed. W. Umbach, 3rd edition, Wiley-VCH, 2004, pp. 235-236. Suitable further thickeners for the preparations according to the invention are described for example also on page 37, line 12 to page 38, line 8 of WO 2006/106140. Reference is hereby made to the contents of the cited passages in their entirety.

In one embodiment of this invention, however, no further thickeners are used besides the polyurethanes according to the invention for preparing the preparations according to the invention.

In a specific embodiment, of the polyurethanes according to the invention, the 10% strength by weight aqueous dispersions thereof having, at a shear rate of 100 l/s, a dynamic viscosity, measured as described below, of at least 100 mPa*s, particularly of at least 200 mPa*s and very particularly of at least 300 mPa*s.

The aqueous dispersions of the polyurethanes obtainable by the process according to one or more embodiments of the invention can exhibit Newtonian or non-Newtonian behavior.

Non-Newtonian 10% strength by weight aqueous dispersions which comprise the polyurethanes obtainable by the process according to one or more embodiments of the invention have, at a shear rate of 100 l/s, dynamic viscosities of at least 1000 mPa*s, particularly of at least 3000 mPa*s.

The person skilled in the art is aware that the effectiveness of many thickeners in aqueous preparations diminishes if the preparations comprise salts or surfactants. By contrast, the polyurethanes according to the invention permit a stable viscosity of aqueous preparations even upon the addition of salts and/or surfactants.

In a specific embodiment of the polyurethanes according to the invention, there is a salt concentration of at least 0.5% by weight following the addition, lead to a stabilization of the dynamic viscosity, measured as described below, of the aqueous preparations comprising them.

In a specific embodiment, to those polyurethanes which permit a stable dynamic viscosity even upon the addition of at least 0.5% by weight of salt and addition of at least 1% by weight of surfactant are used.

In a further specific embodiment, the presence of the polyurethanes according to the invention in salt-containing aqueous preparations leads to an increase in the viscosity compared to preparations which comprise only salt or only polyurethanes according to the invention.

The order in which polyurethane and salt are added is not important here.

In a specific embodiment of the polyurethanes according to the invention, those are used which lead to an increase in the dynamic viscosity of aqueous salt- and/or surfactant-containing preparations.

Polyurethanes according to one specific embodiment of the invention which, in the case of a salt concentration of the aqueous preparation of at least 0.05% by weight, based on the aqueous preparation, lead to an increase in the dynamic viscosity.

Polyurethanes according to an even more specific embodiment of the invention which, in the case of a salt concentration of greater than or equal to 0.5% by weight, based on the aqueous preparation, lead to an increase in the dynamic viscosity.

In certain specific embodiments, the polyurethanes lead to an increase in the dynamic viscosity compared to preparations which comprise less than 0.05% by weight, and in a specific embodiment, less than or equal to 0.01% by weight, of salt, or less than 0.5% by weight, and in a specific embodiment, less than or equal to 0.1% by weight, of surfactant.

A further advantage of the polyurethanes obtainable by the process according to one or more embodiments of the invention is the micelle formation in water. The critical material concentration for micelle formation, also called critical micelle concentration (CMC) indicates the concentration of a substance, in most cases of a substance which has hydrophobic and hydrophilic sections on the inside, at which micelles with an average particle size of less than or equal to 200 nm, in particular less than or equal to 100 nm (determinable by means of dynamic light scattering) are spontaneously formed. In a specific embodiment, the CMC of the polyurethanes according to the invention in water is less than or equal to 1 g/l, particularly less than or equal to 0.5 g/l, especially less than or equal to 0.25 g/l and very particularly less than or equal to 0.1 g/l.

A further advantage of the process according to one or more embodiments of the invention, of the polyurethanes obtainable thereby and of the preparations according to one or more embodiments of the invention is the use of alkali(ne earth) metal carboxylate or zinc carboxylate catalysts and thus the simultaneous omission of cosmetically unacceptable catalysts during the preparation of the polyurethanes.

In the field of cosmetic preparations, the known processes with tin are no longer desired since tin may also be present in the products and preparations resulting therefrom.

Moreover, the use of the alkali(ne earth) metal carboxylates or zinc carboxylates as catalysts permits the in-situ production of allophanate and isocyanurate structures and thus the economically advantageous production of branched hydrophobic sections D of the polyurethanes. By virtue of partially branched sections D, polyurethane thickeners with higher efficiency can be obtained.

On account of their tolerance toward high salt contents and simultaneously high surfactant contents even at extreme pH values, the polyurethanes according to the invention can advantageously also be used as thickeners in homecare preparations, such as, for example, liquid cleaners.

In particular, the polyurethanes according to the invention are also suitable as rheology modifiers for preparations containing hydrogen peroxide.

Cosmetic Preparations

In one or more embodiments of the invention, the polyurethanes obtainable according to the invention are used in cosmetic preparations. The invention thus provides cosmetic preparations comprising the polyurethanes obtainable according to the invention.

One embodiment of the invention is water-comprising cosmetic preparations comprising polyurethanes obtainable according to the invention.

The preparations according to the invention can be in the form of aqueous or aqueous-alcoholic solutions, O/W and W/O emulsions, hydrodispersion formulations, solids-stabilized formulations, stick formulations, PIT formulations, in the form of creams, foams, sprays (pump spray or aerosol), gels, gel sprays, lotions, oils, oil gels or mousses and accordingly be formulated with customary further auxiliaries.

In a specific embodiment, the preparations according to the invention are in the form of a gel, foam, mousse, spray, ointment, cream, emulsion, suspension, lotion, milk or paste.

Another aspect of the invention relates to cosmetic preparations which are selected from gels, gel creams, milks, hydroformulations, stick formulations, cosmetic oils and oil gels, mascara, self-tanning compositions, face care compositions, body care compositions, aftersun preparations. The term cosmetic preparations is also understood as meaning preparations for oral care.

Further cosmetic preparations according to the invention are skin cosmetic preparations, in particular those for caring for the skin. These are present in particular as W/O or, in a particular embodiment, O/W skin creams, day and night creams, eye creams, face creams, antiwrinkle creams, mimic creams, moisturizing creams, bleaching creams, vitamin creams, skin lotions, care lotions and moisturizing lotions.

Further specific examples of preparations according to the invention are face masks, cosmetic lotions and preparations for the use in decorative cosmetics, for example for concealing sticks, stage make-up, mascara and eyeshadows, lipsticks, kohl pencils, eyeliners, make-ups, foundations, blushers, powders and eyebrow pencils.

Further preparations according to the invention are antiacne compositions, repellents, shaving compositions, hair removal compositions, intimate care compositions, foot care compositions and baby care products.

Further specific examples of preparations according to the invention are washing, showering and bathing preparations. Within the context of this invention, washing, showering and bathing preparations are soaps of liquid to gel-like consistency, transparent soaps, luxury soaps, deodorant soaps, cream soaps, baby soaps, skin protection soaps, abrasive soaps and syndets, pasty soaps, soft soaps and washing pastes, liquid washing, showering and bathing preparations, such as washing lotions, shower baths and shower gels, foam baths, oil baths and scrub preparations, shaving foams, shaving lotions and shaving creams.

Cosmetic preparations which comprise specific polyurethanes are described for example in WO 2009/135857. The polyurethanes obtainable according to various embodiments of the invention are generally also suitable for use in the preparations described in WO 2009/135857. Reference is hereby made expressly to the disclosure in WO 2009/135857.

Within the context of the present invention, the polyurethanes used in the preparations of WO 2009/135857 are replaced by the polyurethanes of this invention. The polyurethanes according to the invention may thus be used in the preparations of WO 2009/135857 in place of the polyurethanes used therein.

Suitable ingredients for the preparations according to the invention are described in WO 2009/135857, p. 24 to p. 35, to which reference is made in its entirety.

Cosmetic UV photoprotective compositions comprising the polyurethanes obtained according to the invention are also in accordance with the invention. Within the context of this invention, cosmetic photoprotective compositions are understood as meaning cosmetic preparations which comprise at least one, and in a specific embodiment, two or more, UV filter substances.

UV photoprotective compositions corresponding to the UV photoprotective composition preparations according to the invention are described in WO 2009/135857, p. 35 to p. 42, to which reference is made in its entirety.

The invention also relates to cosmetic preparations, and in a specific embodiment, in liquid or pasty form, for use on the skin, on semi mucosa, on mucosa and in particular on keratin materials such as hair, eyelashes and eyebrows, in particular for the shaping, decoration, coloring, beautifying of the same, and also for caring for the skin and the skin appendages. In principle, the preparations according to the invention, upon suitable adjustment and coloring, can also be used as make-up, concealer, camouflage, eyeshadows, eyeliners, lip liners, blushers, lip blush, lip gloss, sun protection composition, sun block, temporary tattoo, colored effect sunscreen for surfers and the like.

A specific embodiment of the present invention is thus cosmetic preparations for decorative cosmetics.

Preparations corresponding to the preparations according to the invention for decorative cosmetics are described in WO 2009/135857, p. 43 to p. 46, to which reference is made in its entirety.

Various embodiments of the present invention provide aqueous preparations which, besides the polyurethanes obtainable according to the invention, further comprise at least one salt or surfactant or both.

A further embodiment of the invention is shampoos and cosmetic cleaning compositions comprising the polyurethanes obtainable according to the invention.

Preparations corresponding to the shampoos and cosmetic cleaning compositions according to the invention are described analogously in WO 2009/135857, p. 46 to p. 55, to which reference is made in its entirety.

A further embodiment of the invention is deodorants or antiperspirants, in particular deodorant lotions and deodorant or antiperspirant sticks, comprising the polyurethanes obtainable according to the invention and based on oil-in-water dispersion or emulsion for the application of active ingredients, in particular of water-soluble active ingredients, to the skin.

Preparations corresponding to the deodorants and antiperspirants according to the invention are described analogously in WO 2009/135857, p. 55 to p. 59, to which reference is made in its entirety.

A further embodiment of the invention is hair colorants comprising the polyurethanes obtainable according to the invention.

Preparations corresponding to the hair colorants comprising the polyurethanes obtainable according to the invention are described analogously in WO 2009/135857, p. 59 to p. 65, to which reference is made in its entirety.

A further embodiment of the invention is hair care compositions, in particular hair conditioners, comprising the polyurethanes obtainable according to the invention.

Hair care compositions corresponding to the hair care compositions comprising the polyurethanes obtainable according to the invention are described analogously in WO 2009/135857, p. 59 to p. 67, to which reference is made in its entirety.

A further embodiment of the invention is acidic preparations comprising the polyurethanes obtainable according to the invention.

Numerous cosmetic preparations comprise active ingredients which develop their desired effect in particular at acidic pHs. These include, for example, preparations which comprise alpha-hydroxycarboxylic acids (AHAs) and beta-hydroxycarboxylic acids (BHAs) since these are not effective or not very effective in the neutralized state. Acidic preparations corresponding to the acidic preparations comprising the polyurethanes obtainable according to the invention are described analogously in WO 2009/135857, p. 67 to p. 69, to which reference is made in its entirety.

A further embodiment of the invention is self-tanning products comprising the polyurethanes obtainable according to the invention.

Standard commercial self-tanning products are generally 0/W emulsions. In these, the water phase is stabilized by emulsifiers customary in cosmetics.

By applying the self-tanning products according to the invention, it is possible to achieve not only a uniform skin coloration, but it is also possible to uniformly color areas of skin that are differently colored by nature or as a result of a pathological change.

According to one or more embodiments of the invention, the self-tanning substances used are advantageously inter alia glycerol aldehyde, hydroxymethylglyoxal, γ-dialdehyde, erythrulose, 5-hydroxy-1,4-naphtoquinone (juglone), and also 2-hydroxy-1,4-naphtoquinine as occurs in henna leaves. In a specific embodiment, the self-tanning substance is 1,3-dihydroxyacetone (DHA), a trivalent sugar which occurs in the human body. 6-Aldo-D-fructose and ninhydrin can also be used as self-tanning agents according to the invention. For the purposes of the invention, self-tanning agents are also understood as meaning substances which bring about a skin coloration other than a brown shade.

In one specific embodiment of the invention, such preparations comprise self-tanning substances in a concentration of from 0.1 to 10% by weight, and in an even more specific embodiment, from 0.5 to 6% by weight, in each case based on the total weight of the preparation.

In a specific embodiment, these preparations comprise 1,3-dihydroxyacetone as self-tanning substance. These compositions further may comprise organic and/or inorganic light protection filters. The preparations can also comprise inorganic and/or organic and/or modified inorganic pigments.

Further ingredients which may be present in the preparations according to one or more embodiments of the invention are specified, for example, in DE 103 21 147 in paragraphs [0024] to [0132], to which reference is made at this point in their entirety.

The invention also provides the use of such preparations for coloring the skin of multicellular organisms, in particular the skin of humans and animals, especially for harmonizing the color of differently pigmented areas of skin.

A further embodiment of the invention is preparations for oral and dental care and cleansing which comprise the polyurethanes obtainable according to the invention.

Preparations corresponding to the preparations for oral and dental care and cleansing comprising the polyurethanes obtainable according to the invention are described analogously in WO 2009/135857, p 0.69 to p. 70, to which reference is made in its entirety.

A further embodiment of the invention is preparations for hair removal which comprise the polyurethanes obtainable according to the invention.

Preparations corresponding to the preparations for hair removal which comprise the polyurethanes obtainable according to the invention are described analogously in WO 2009/135857, p. 70 to p. 71, to which reference is made in its entirety.

A further embodiment of the invention is preparations for permanent hair shaping comprising the polyurethanes obtainable according to the invention.

Preparations corresponding to the preparations for permanent hair shaping which comprise the polyurethanes obtainable according to the invention are described analogously in WO 2009/135857, p. 71 to p. 73, to which reference is made in its entirety.

EXAMPLES

The invention is illustrated in more detail by reference to the nonlimiting examples below.

Unless stated otherwise, the percentages are percentages by weight.

Determination of the Dynamic Viscosity

The dynamic viscosities of the polyurethanes according to the invention were measured in the form of a 10 percent strength by weight aqueous dispersion at 23° C. In the examples listed below, the dynamic viscosity was always determined at shear rates of 100 1/s and 350 1/s. These two values allow a statement about whether the polyurethanes according to the invention exhibit non-Newtonian or Newtonian thickener behavior in aqueous dispersion.

To determine the dynamic viscosity to DIN 53019, the following were used:

rotary viscometer Physica Rheolab MCI Portable (Anton Paar);

cylinder measurement system, Z4 DIN cylinder (diameter 14 mm).

The polyols, ethoxylated alcohols and isocyanates used below were used in essentially alkali-free form. The ppm data for potassium and/or zinc refer in each case to the total amount of substances reactive towards isocyanate groups plus the corresponding potassium carboxylate or zinc carboxylate.

Synthesis Example 1

Preparation of a PUR Associative Thickener A.1

Catalyst: 300 ppm of K as Potassium Acetate 120.00 g of polyethylene glycol Pluriol®E6000 (BASF SE, molecular weight 6000 g/mol), 9.60 g of Lutensol® TO10 (BASF SE), 11.10 g of Lutensol® AT11 (BASF SE), and 106 mg of potassium acetate (=300 ppm of potassium) were introduced as initial charge under nitrogen in a 2 liter polymerization reactor and then heated to 100° C. By applying a vacuum of ca. 10 mbar for 6 hours, traces of water were removed until ultimately the water content of the mixture was 230 ppm. The mixture was then cooled to 80° C. By adding 5.88 g of hexamethylene diisocyanate, the polymerization was started and the mixture was stirred at a temperature of 80° C. for 50 minutes until an isocyanate content of 0.0% was reached. The yellow colored residue was then dissolved in 586.3 g of water and the aqueous solution was immediately admixed with 7.33 g of Euxyl® K701 (Schülke & Mayr) and 70 mg of the stabilizer 4-hydroxy-TEMPO. The mixture was cooled to room temperature (25° C.). The polymer A.1 ($M_n$=11 700 g/mol; $M_w$=26 900 g/mol) was thus obtained in the form of a clear, pale yellow colored solution which had a solids content of 20.8%. The viscosity of a 10% strength by weight aqueous solution of the polyether polyurethane A.1 was 1550 mPa*s (shear rate 100 l/s) and 1360 mPa*s (shear rate 350 l/s).

Synthesis Example 2

Preparation of a PUR Associative Thickener A.2

Catalyst: 600 ppm of K as Potassium Acetate 120.00 g of polyethylene glycol Pluriol®E6000, 9.60 g of Lutensol® TO10, 11.10 g of Lutensol® AT11, and 212 mg of potassium acetate (=600 ppm of potassium) were introduced as initial charge under nitrogen in a 2 l polymerization reactor and then heated to 100° C. By applying a vacuum of ca. 10 mbar for 5 hours, traces of water were removed until ultimately the water content of the mixture was 225 ppm. The mixture was then cooled to 80° C. By adding 5.88 g of hexamethylene diisocyanate, the polymerization was started and the mixture was stirred at a temperature of 80° C. for 50 minutes until an isocyanate content of 0.0% was reached. The yellow colored residue was then dissolved in 586.3 g of water and the aqueous solution was immediately admixed with 7.33 g of Euxyl® K701 and 70 mg of the stabilizer 4-hydroxy-TEMPO. The mixture was cooled to room temperature (25° C.). The polymer A.2 ($M_n$=12 300 g/mol; $M_w$=29 700 g/mol) was thus obtained in the form of a clear, pale yellow colored solution which had a solids content of 20.1%. The viscosity of a 10% strength by weight aqueous solution of the polyether polyurethane A.2 was 3700 mPa*s (shear rate 100 l/s) and 3000 mPa*s (shear rate 350 l/s).

Synthesis Example 3

Preparation of a PUR Associative Thickener A.3

Catalyst: 900 ppm of K as Potassium Acetate 120.00 g of polyethylene glycol Pluriol®E6000, 9.60 g of Lutensol® TO10, 11.10 g of Lutensol® AT11, and 318 mg of potassium acetate (=900 ppm of potassium) were introduced as initial charge under nitrogen in a 2 l polymerization reactor and then heated to 100° C. By applying a vacuum of ca. 10 mbar for 4 hours, traces of water were removed until ultimately the water content of the mixture was 242 ppm. The mixture was then cooled to 80° C. By adding 5.88 g of hexamethylene diisocyanate, the polymerization was started and the mixture was stirred at a temperature of 80° C. for 55 minutes until an isocyanate content of 0.0% was reached. The yellow colored residue was then dissolved in 586.3 g of water and the aqueous solution was immediately admixed with 7.33 g of the preservative Euxyl® K701 and 70 mg of the stabilizer 4-hydroxy-TEMPO. The mixture was cooled to room temperature (25° C.). The polymer A.3 ($M_n$=12 700 g/mol; $M_w$=33 000 g/mol) was thus obtained in the form of a clear, pale yellow colored solution which had a solids content of 20.6%. The viscosity of a 10% strength by weight aqueous solution of the polyether polyurethane A.3 was 6000 mPa*s (shear rate 100 l/s) and 4400 mPa*s (shear rate 350 l/s).

Synthesis Example 4

Preparation of a PUR Associative Thickener A.4

Catalyst: 2000 ppm of K as Potassium Acetate 90.00 g of polyethylene glycol Pluriol®E6000, 7.20 g of Lutensol® TO10, 8.33 g of Lutensol® AT11, and 530 mg of potassium acetate (=2000 ppm of potassium) were introduced as initial charge under nitrogen in a 2 l polymerization reactor and then heated to 100° C. By applying a vacuum of ca. 10 mbar for 5 hours, traces of water were removed until ultimately the water content of the mixture was 210 ppm. The mixture was then cooled to 80° C. By adding 4.41 g of hexamethylene diisocyanate, the polymerization was started and the mixture was stirred at a temperature of 80° C. for 55 minutes until an isocyanate content of 0.0% was reached. The yellow colored residue was then dissolved in 439.7 g of water and the aqueous solution was immediately admixed with 5.50 g of the preservative Euxyl® K701 and 50 mg of the stabilizer 4-hydroxy-TEMPO. The mixture was cooled to room temperature (25° C.). The polymer A.4 ($M_n$=12 500 g/mol; $M_w$=31 300 g/mol) was thus obtained in the form of a clear, pale yellow colored solution which had a solids content of 20.6%. The viscosity of a 10% strength by weight aqueous solution of the polyether polyurethane A.4 was 5200 mPa*s (shear rate 100 l/s) and 3800 mPa*s (shear rate 350 l/s).

Synthesis Example 5

Preparation of a PUR Associative Thickener A.5

Catalyst: 200 ppm of K as Potassium Acetate 100.00 g of polyethylene glycol (Merck KGaA, molecular weight 10 000 g/mol), 10.02 g of 2-decyl-1-tetradecanol-20 EO, and 55 mg of potassium acetate (=200 ppm of potassium) were introduced as initial charge under nitrogen in a 2 l polymerization reactor and then heated to 100° C. By applying a vacuum of ca. 10 mbar for 6 hours, traces of water were removed until ultimately the water content of the mixture was 190 ppm. The mixture was then cooled to 80° C. By adding 2.52 g of hexamethylene diisocyanate, the polymerization was started and the mixture was stirred at a temperature of 80° C. for 40 minutes until an isocyanate content of 0.0% was reached. The yellow colored residue was then dissolved in 450.2 g of water and the aqueous solution was immediately admixed with 5.63 g of the preservative Euxyl® K701 and 60 mg of the stabilizer 4-hydroxy-TEMPO. The mixture was cooled to room temperature (25° C.). The polymer A.5 ($M_n$=19 100 g/mol; $M_w$=48 500 g/mol) was thus obtained in the form of a clear, pale yellow colored solution which had a solids content of 20.7%. The viscosity of a 5% strength by weight aqueous solution of the polyether polyurethane A.5 was >20 000 mPa*s (shear rate 100 l/s) and >20 000 mPa*s (shear rate 350 l/s).

Synthesis Example 6

Preparation of a PUR Associative Thickener A.6

Catalyst: Zinc Neodecanoate; Single-Stage Reaction 120.00 g of polyethylene glycol Pluriol®E6000 (BASF SE, molecular weight 6000 g/mol), dealkylated, 9.60 g of Lutensol® TO10 (BASF SE), dealkylated, and 11.10 g of Lutensol® AT11 (BASF SE), dealkylated, were introduced as initial charge under nitrogen in a 2 l polymerization reactor and then heated to 100° C. By applying a vacuum of ca. 10 mbar for 6 hours, traces of water were removed until ultimately the water content of the mixture was 200 ppm. The mixture was then cooled to 80° C. The mixture was admixed with 675 mg of TIB® Kat 616 (TIB Chemicals, Mannheim; =zinc neodecanoate, dissolved in a mixture of aliphatic hydrocarbons; =900 ppm of zinc). By adding 5.88 g of hexamethylene diisocyanate, the polymerization was started and the mixture was stirred at a temperature of 80° C. for 40 minutes until an isocyanate content of 0.0% was reached. The yellow colored residue was then dissolved in 589.0 g of water and the aqueous solution was immediately admixed with 7.36 g of the preservative Euxyl® K701 (Schülke & Mayr) and 70 mg of the stabilizer 4-hydroxy-TEMPO. The mixture was cooled to room temperature (25° C.). The polymer A.1 ($M_n$=11 200 g/mol; $M_w$=26 400 g/mol) was thus obtained in the form of a clear, pale yellow colored solution which had a solids content of 21.0%. The viscosity of a 10% strength by weight aqueous solution of the polyether polyurethane A.6 was 2550 mPa*s (shear rate 100 l/s) and 2050 mPa*s (shear rate 350 l/s).

Comparative Example 1

Preparation of a PUR Associative Thickener A.7

Without Catalyst, Single-Stage Reaction 120.00 g of polyethylene glycol Pluriol®E6000, 9.60 g of Lutensol® TO10, and 11.10 g of Lutensol® AT11 were introduced as initial charge under nitrogen in a 2 l polymerization reactor and then heated to 100° C. By applying a vacuum of ca. 10 mbar for 5 hours, traces of water were removed until ultimately the water content of the mixture was 250 ppm. The mixture was then cooled to 80° C. By adding 5.88 g of hexamethylene diisocyanate, the polymerization was started and the mixture was stirred at a temperature of 80° C. for a total of 32 hours until an isocyanate content of 0.0% was reached. The yellow colored residue was then dissolved in 586.3 g of water and the aqueous solution was immediately admixed with 7.33 g of the preservative Euxyl® K701 and 70 mg of the stabilizer 4-hydroxy-TEMPO. The mixture was cooled to room temperature (25° C.). The polymer A.6 ($M_n$=10 000 g/mol; $M_w$=23 200 g/mol) was thus obtained in the form of a clear, pale yellow colored solution which had a solids content of 18.8%. The viscosity of a 10% strength by weight aqueous solution of the polyether polyurethane A.7 was 100 mPa*s (shear rate 100 l/s) and 100 mPa*s (shear rate 350 l/s).

Comparative Example 2

Preparation of a PUR Associative Thickener A.8

Without Catalyst, Single-Stage Reaction 100.00 g of polyethylene glycol (Merck KGaA, molecular weight 10 000 g/mol), and 10.02 g of 2-decyl-1-tetradecanol-20 EO were introduced as initial charge under nitrogen in a 2 l polymerization reactor and then heated to 100° C. By applying a vacuum of ca. 10 mbar for 6 hours, traces of water were removed until ultimately the water content of the mixture was 185 ppm. The mixture was then cooled to 80° C. By adding 2.52 g of hexamethylene diisocyanate, the polymerization was started and the mixture was stirred at a temperature of 80° C. for a total of 12 hours until an isocyanate content of 0.0% was reached. The yellow colored residue was then dissolved in 450.2 g of water and the aqueous solution was immediately admixed with 5.63 g of the preservative Euxyl® K701 and 60 mg of the stabilizer 4-hydroxy-TEMPO. The mixture was cooled to room temperature (25° C.). The polymer A.7 ($M_n$=5200 g/mol; $M_w$=14 500 g/mol) was thus obtained in the form of a clear, pale yellow colored solution which had a solids content of 18.5%. The viscosity of a 10% strength by weight aqueous solution of the polyether polyurethane A.8 was <100 mPa*s (shear rate 100 l/s) and <100 mPa*s (shear rate 350 l/s).

Comparative Example 3

Preparation of a PUR Associative Thickener A.9

Catalyst: Dibutyltin Dilaurate, Single-Stage Reaction 90.00 g of polyethylene glycol Pluriol®E6000, 7.20 g of Lutensol® TO10, 8.33 g of Lutensol® AT11, and 144 mg of dibutyltin dilaurate (DBTL) (=300 ppm of Sn based on total mixture) were introduced as initial charge under nitrogen in a 2 l polymerization reactor and then heated to 100° C. By applying a vacuum of ca. 10 mbar for 5 hours, traces of water were removed until ultimately the water content of the mixture was 250 ppm. The mixture was then cooled to 80° C. By adding 4.41 g of hexamethylene diisocyanate, the polymerization was started and the mixture was stirred at a temperature of 80° C. for 60 minutes until an isocyanate content of 0.0% was reached. The yellow colored residue was then dissolved in 440.3 g of water and the aqueous solution was immediately admixed with 5.50 g of the preservative Euxyl® K701 and 60 mg of the stabilizer 4-hydroxy-TEMPO. The mixture was cooled to room temperature (25° C.). The polymer A.8 ($M_n$=10 100 g/mol; $M_w$=22 000 g/mol) was thus obtained in the form of a clear, pale yellow colored solution which had a solids content of 20.4%. The viscosity of a 10% strength by weight aqueous solution of the polyether polyurethane A.9 was 720 mPa*s (shear rate 100 l/s) and 660 mPa*s (shear rate 350 l/s).

Comparative Example 4

Preparation of a PUR Associative Thickener A.10

Catalyst: DABCO, Single-Stage Reaction 120.00 g of polyethylene glycol Pluriol®E6000, 9.60 g of Lutensol® TO10, 11.10 g of Lutensol® AT11, and 36 mg of 1,4-diazabicyclo[2.2.2]octane (DABCO; =300 ppm based on total mixture) were introduced as initial charge under nitrogen in a 2 l polymerization reactor and then heated to 100° C. By applying a vacuum of ca. 10 mbar for 5 hours, traces of water were removed until ultimately the water content of the mixture was 230 ppm. The mixture was then cooled to 80° C. By adding 5.88 g of hexamethylene diisocyanate, the polymerization was started and the mixture was stirred at a temperature of 80° C. for a total of 13 hours until an isocyanate content of 0.0% was reached. The yellow colored residue was then dissolved in 586.5 g of water and the aqueous solution was immediately admixed with 7.33 g of the preservative Euxyl® K701 and 70 mg of the stabilizer 4-hydroxy-TEMPO. The mixture was cooled to room temperature (25° C.). The polymer A.9 ($M_n$=8500 g/mol; $M_w$=17 400 g/mol) was thus obtained in the form of a clear, pale yellow colored solution which had a solids content of 18.7%. The viscosity of a 10% strength by weight aqueous solution of the polyether polyurethane A.10 was 105 mPa*s (shear rate 100 l/s) and 105 mPa*s (shear rate 350 l/s).

Comparative Example 5

Preparation of a PUR Associative Thickener A.11

Catalyst: Zinc Neodecanoate; Two-Stage Reaction 120.00 g of polyethylene glycol Pluriol®E6000 (BASF SE, molecular weight 6000 g/mol) were dissolved in 467.00 g of xylene under nitrogen in a 2 l polymerization reactor (flat flange glass vessel with anchor stirrer). After heating the solution to ca. 140° C. (internal temperature), exactly 200 g of xylene were distilled off. The water content of the reaction mixture was then only still ca. 50 ppm. The polymer solution was then cooled to 50° C. (internal temperature) and admixed with 107 mg of acetic acid, dissolved in 5 ml of xylene, in order to neutralize the amount of potassium acetate, determined in quantitative terms beforehand, within the polyethylene glycol. By adding 360 mg of TIB Kat 616 (TIB Chemicals, Mannheim; =zinc neodecanoate, dissolved in a mixture of aliphatic hydrocarbons; =400 ppm of zinc based on total mixture), dissolved in 5 ml of xylene, and 5.88 g of hexamethylene diisocyanate, dissolved in 10 ml of xylene, the polymerization was started and the mixture was run at an internal temperature of 50° C. to an isocyanate content of 0.25%. A mixture of 9.60 g of Lutensol® TO10 (BASF SE) and 11.10 g of Lutensol® AT11 (BASF SE), dissolved in 20 ml of xylene, was then added and the reaction mixture was further heated at 50° C. until the isocyanate content was 0%. The solvent xylene was then largely removed by vacuum distillation at elevated temperature (60° C.) (residual content<100 ppm) and the residue was dissolved in 586.3 g of water. After cooling to room temperature (25° C.), finally, 3.67 g of the preservative Euxyl® K500 were added to the aqueous solution. The polymer A.11 ($M_n$=17 700 g/mol; $M_w$=31 800 g/mol) was obtained in the form of an aqueous dispersion which had a solids content of 19.8%. The viscosity of a 10% strength by weight aqueous solution of the polyether polyurethane A.11 was 6400 mPa*s (shear rate 100 l/s) and 4600 mPa*s (shear rate 350 l/s).

Formulation Example 1

Cosmetic Formulations Based on Cremophor® A6/Cremophor® A25

The cosmetic formulations were prepared by adding the water phase B to the oil phase A and then admixing the resulting O/W emulsion with the preservative (phase C). This gave the following formulations based on a Cremophor® A6/Cremophor® A25 base.

TABLE 1

Formulations based on Cremophor ® A6/Cremophor ® A25

| Phase | Ingredients | F.1.1 | F.1.2 | F.1.3 | F.1.4 | F.1.5 |
|---|---|---|---|---|---|---|
| Phase A | Cremophor ® A 6 | 2.0 g | 2.0 g | 2.0 g | 2.0 g | 2.0 g |
| | Cremophor ® A 25 | 2.0 g | 2.0 g | 2.0 g | 2.0 g | 2.0 g |
| | Lanette ® O | 2.5 g | 2.5 g | 2.5 g | 2.5 g | 2.5 g |
| | Paraffin oil | 5.0 g | 5.0 g | 5.0 g | 5.0 g | 5.0 g |
| | Luvitol ® EHO | 5.0 g | 5.0 g | 5.0 g | 5.0 g | 5.0 g |
| Phase B | PUR thickener | A.1 0.5 g | A.2 0.5 g | A.3 0.5 g | A.4 0.5 g | A.5 0.5 g |
| | 1,2-Propylene glycol | 5.0 g | 5.0 g | 5.0 g | 5.0 g | 5.0 g |
| | Water | 77.5 g | 77.5 g | 77.5 g | 77.5 g | 77.5 g |
| Phase C | Euxyl ® K300 | 0.5 g | 0.5 g | 0.5 g | 0.5 g | 0.5 g |

TABLE 2

Formulations based on Cremophor ® A6/Cremophor ® A25

| Phase | Ingredients | F.1.7 | F.1.8 | F.1.9 | F.1.10 |
|---|---|---|---|---|---|
| Phase A | Cremophor ® A 6 | 2.0 g | 2.0 g | 2.0 g | 2.0 g |
| | Cremophor ® A 25 | 2.0 g | 2.0 g | 2.0 g | 2.0 g |
| | Lanette ® O | 2.5 g | 2.5 g | 2.5 g | 2.5 g |
| | Paraffin oil | 5.0 g | 5.0 g | 5.0 g | 5.0 g |
| | Luvitol ® EHO | 5.0 g | 5.0 g | 5.0 g | 5.0 g |
| Phase B | PUR thickener | A.7 0.5 g | A.8 0.5 g | A.9 0.5 g | A.10 0.5 g |
| | 1,2-Propylene glycol | 5.0 g | 5.0 g | 5.0 g | 5.0 g |
| | Water | 77.5 g | 77.5 g | 77.5 g | 77.5 g |
| Phase C | Euxyl ® K300 | 0.5 g | 0.5 g | 0.5 g | 0.5 g |

Formulation Example 2

Cosmetic Formulations Based on Stearate Ester

The cosmetic formulations were prepared by adding the water phase B to the oil phase A and subsequently admixing the resulting O/W emulsion with the preservative (phase C). This gave the following formulations based on a stearate ester base.

TABLE 3

Formulations based on stearate ester

| Phase | Ingredients | F.2.1 | F.2.2 | F.2.3 | F.2.4 | F.2.5 |
|---|---|---|---|---|---|---|
| Phase A | Cutina ® GMS | 2.0 g | 2.0 g | 2.0 g | 2.0 g | 2.0 g |
| | Lanette ® 18 | 2.0 g | 2.0 g | 2.0 g | 2.0 g | 2.0 g |
| | Dow Corning 345 Fluid | 3.0 g | 3.0 g | 3.0 g | 3.0 g | 3.0 g |
| | Cetiol ® OE | 3.0 g | 3.0 g | 3.0 g | 3.0 g | 3.0 g |
| | Abil ® 350 | 2.0 g | 2.0 g | 2.0 g | 2.0 g | 2.0 g |
| | Dry Flo PC | 1.0 g | 1.0 g | 1.0 g | 1.0 g | 1.0 g |
| | Myrj 52 | 2.0 g | 2.0 g | 2.0 g | 2.0 g | 2.0 g |
| Phase B | PUR thickener | A.1 0.5 g | A.2 0.5 g | A.3 0.5 g | A.4 0.5 g | A.5 0.5 g |
| | Glycerol | 5.0 g | 5.0 g | 5.0 g | 5.0 g | 5.0 g |
| | Water | 79.0 g | 79.0 g | 79.0 g | 79.0 g | 79.0 g |
| Phase C | Euxyl ® K300 | 0.5 g | 0.5 g | 0.5 g | 0.5 g | 0.5 g |

TABLE 4

Formulations based on stearate ester

| Phase | Ingredients | F.2.7 | F.2.8 | F.2.9 | F.2.10 |
|---|---|---|---|---|---|
| Phase A | Cutina ® GMS | 2.0 g | 2.0 g | 2.0 g | 2.0 g |
| | Lanette ® 18 | 2.0 g | 2.0 g | 2.0 g | 2.0 g |
| | Dow Corning 345 Fluid | 3.0 g | 3.0 g | 3.0 g | 3.0 g |
| | Cetiol ® OE | 3.0 g | 3.0 g | 3.0 g | 3.0 g |
| | Abil ® 350 | 2.0 g | 2.0 g | 2.0 g | 2.0 g |
| | Dry Flo PC | 1.0 g | 1.0 g | 1.0 g | 1.0 g |
| | Myrj 52 | 2.0 g | 2.0 g | 2.0 g | 2.0 g |
| Phase B | PUR thickener | A.7 0.5 g | A.8 0.5 g | A.9 0.5 g | A.10 0.5 g |

TABLE 4-continued

Formulations based on stearate ester

| Phase | Ingredients | F.2.7 | F.2.8 | F.2.9 | F.2.10 |
|---|---|---|---|---|---|
| | Glycerol | 5.0 g | 5.0 g | 5.0 g | 5.0 g |
| | Water | 79.0 g | 79.0 g | 79.0 g | 79.0 g |
| Phase C | Euxyl ® K300 | 0.5 g | 0.5 g | 0.5 g | 0.5 g |

Viscosities as a Function of the Salt Concentration

TABLE 3

| Formulation | Viscosity [mPa * s] with 2.0% NaCl addition |
|---|---|
| F.1.1 | 12 100 |
| F.1.2 | 17 100 |
| F.1.3 | 26 200 |
| F.1.4 | 17 000 |
| F.1.7 | 6800 |
| F.1.9 | 11 400 |

Viscosities as a Function of the Salt Concentration

TABLE 4

| Formulation | Viscosity [mPa * s] with 2.0% NaCl addition |
|---|---|
| F.2.1 | 16 700 |
| F.2.2 | 21 800 |
| F.2.3 | 21 200 |
| F.2.4 | 18 100 |
| F.2.7 | 10 000 |
| F.2.9 | 14 700 |

Viscosities as a Function of Shear Rate and Concentration

TABLE 5

| Polymer | Polymer concentration in water [% by weight] | Viscosity [mPa * s] Shear rate 100 1/s | Viscosity [mPa * s] Shear rate 350 1/s |
|---|---|---|---|
| A.1 | 10 | 1550 | 1360 |
| A.2 | 10 | 3700 | 3000 |
| A.3 | 10 | 6000 | 4400 |
| A.4 | 10 | 5200 | 3800 |
| A.5 | 5 | >20 000 | >20 000 |
| A.7 | 10 | 100 | 100 |
| A.8 | 10 | <100 | <100 |
| A.9 | 10 | 720 | 660 |
| A.10 | 10 | 105 | 105 |

FIG. 1 shows the GPC chromatograms of the two thickeners A.5 and A.8.

The solid line in FIG. 1 represents A.5 (according to the invention, 200 ppm of K as KOAc): high molar mass, and the dashed line represents A.8 (not according to the invention, without KOAc): low molar mass.

Formulation Example 3

Cosmetic Formulations with Associative Thickeners A.6 and A.11

The cosmetic formulations were prepared by adding the water phase B to the oil phase A and subsequently admixing the resulting O/W emulsion with the preservative (phase C). This gave the following formulations based on a Cremophor® A6/Cremophor® A25 basis (Tab. 8).

TABLE 8

Cosmetic formulations based on Cremophor ® A6/A25

| Phase | Ingredients | F.1.6 | F.1.11 |
|---|---|---|---|
| Phase A | Cremophor A 6 | 2.0 g | 2.0 g |
| | Cremophor A 25 | 2.0 g | 2.0 g |
| | Lanette O | 2.5 g | 2.5 g |
| | Paraffin oil | 5.0 g | 5.0 g |
| | Luvitol EHO | 5.0 g | 5.0 g |
| Phase B | PUR thickener | A.6 0.5 g | A.11 0.5 g |
| | 1,2-Propylene glycol | 5.0 g | 5.0 g |
| | Water | 77.5 g | 77.5 g |
| Phase C | Euxyl K300 | 0.5 g | 0.5 g |

Formulation Example 4

Cosmetic Formulations with Associative Thickeners A.6. and A.11

The cosmetic formulations were prepared by adding the water phase B to the oil phase A and subsequently admixing the resulting O/W emulsion with the preservative (phase C). This gave the formulations F.2.6 and CF.2.5 based on a stearate ester base (Tab. 9).

TABLE 9

Formula parameters for the cosmetic formulations F.2.6 and F.2.11 based on a stearate ester base.

| Phase | Ingredients | F.2.6 | F.2.11 |
|---|---|---|---|
| Phase A | Cutina GMS | 2.0 g | 2.0 g |
| | Lanette 18 | 2.0 g | 2.0 g |
| | Dow Corning 345 Fluid | 3.0 g | 3.0 g |
| | Cetiol OE | 3.0 g | 3.0 g |
| | Abil 350 | 2.0 g | 2.0 g |
| | Dry Flo PC | 1.0 g | 1.0 g |
| | Myrj 52 | 2.0 g | 2.0 g |
| Phase B | PUR thickener | A.6 0.5 g | A.11 0.5 g |
| | Glycerol | 5.0 g | 5.0 g |
| | Water | 79.0 g | 79.0 g |
| Phase C | Euxyl K300 | 0.5 g | 0.5 g |

Viscosities and Properties of the Cosmetic Formulations

TABLE 10

Viscosities of the cosmetic formulations admixed with 2% NaCl.

| Formulation | Viscosity [Pa * s] | Properties |
|---|---|---|
| F.1.6 | 14.0 | Polymer dissolved to give a clear solution in the water phase (B), not sticky |
| F.1.11 | 18.0 | Polymer dissolved to give a cloudy solution in the water phase (B), sticky |
| F.2.6 | 22.2 | Polymer dissolved to give a clear solution in the water phase (B), not sticky |
| F.2.11 | 18.7 | Polymer dissolved to give a cloudy solution in the water phase (B), sticky |

For comparable thickening properties, the structure obtainable with polyurethane A.6 can always be better processed (water-soluble to give a clear solution, nonsticky polymer) as polyurethane A.11.

Application Examples

At this point, reference is made in full to the application examples which are disclosed in WO 2009/135857 on pages 87 to 114.

The polyurethanes PU.1 to PU.11 used in the examples therein are replaced for the purposes of this invention by the polyurethanes A.1, A.2, A.3, A.4, A.5 or A.6 obtainable according to the invention, thus giving the corresponding cosmetic preparations.

Further typical preparations according to the invention are described below, without, however, limiting the invention to these examples.

Besides the preparation of the cosmetic preparations described here, the polyurethanes A.1, A.2, A.3, A.4, A.5 or A.6 and also combinations thereof can be added to the resulting emulsion also after combining the water phase and oil phase at 60-80° C. or to the cooled emulsion at about 40° C.

The invention also provides the subsequent addition of the polyurethanes obtainable according to the invention to a cosmetic preparation in order to establish the desired viscosity.

Unless expressly described otherwise, the percentages are % by weight.

O/W Emulsion

| Phase | Ingredient/INCI | F.3.1 | F.3.2 | F.3.3 | F.3.4 | F.3.5 |
|---|---|---|---|---|---|---|
| A | Aqua | ad 100 | ad 100 | ad 100 | ad 100 | ad 100 |
|   | Glycerin | 3.0 | 5.50 | 4.50 | 5.00 | 3.5 |
|   | PUR thickener A.1 | 3.0 | 1.5 | 0.8 | 2.0 | 2.5 |
|   | Hydroxyethyl Acrylate/Sodium Acryloyldimethyl Taurate Copolymer, Squalane, Polysorbate 60 |  | 1.0 |  | 0.5 |  |
| B | Glyceryl Stearate Citrate | 1.80 | 2.00 | 3.00 | 1.50 | 2 |
|   | Sucrose Stearate | 1.00 | 1.20 | 2.00 | 2.20 | 1.5 |
|   | Cetearyl Alcohol | 1.80 | 2.00 | 1.50 | 2.40 | 2.8 |
|   | Ethylhexyl Palmitate | 6.00 | 5.00 | 3.50 | 3.00 | 5.5 |
|   | Caprylic/Capric Triglyceride | 5.00 | 5.00 | 1.00 | 2.00 | 3.5 |
|   | Octyldodecanol | 1.50 | 3.00 | 2.40 | 5.0 | 4.6 |
|   | Dimethicone | 0.20 | 0.50 | 2.00 | 1.80 | 1.4 |
| C | Ammonium Acryloyldimethyltaurate/VP Copolymer |  |  | 0.5 | 0.1 |  |
|   | Carbomer | 0.05 |  |  |  | 0.1 |
| D | Sodium Hydroxide | 0.02 |  |  |  | 0.04 |
| E | Bisabolol | 0.5 | 0.3 | 0.20 | 0.35 | 1.0 |
|   | Phenoxyethanol, paraben mixture | 1.00 | 0.60 | 0.70 | 0.60 | 0.5 |
|   | Perfume | 0.05 | 0.10 | 0.10 | 0.05 | 0.05 |

Preparation:

Heat phases A and B separately to ca. 80° C. Stir phase C into phase B and then stir phase A into phase B/C and briefly homogenize.

Add phase D (when required) and cool with stirring to ca. 40° C. Add components of phase E to the emulsion in succession and cool with stirring to room temperature. Briefly homogenize.

Instead of the O/W emulsion comprising polyurethane thickener A.1, O/W emulsions comprising one or more of the polyurethanes A.2, A.3, A.4, A.5 or A.6 are also prepared.

Hydrodispersion

| Phase | Ingredients/INCI | F.4.1 | F.4.2 | F.4.3 | F.4.4 | F.4.5 |
|---|---|---|---|---|---|---|
| A | Stearyl alcohol | 0.5 | 1.5 |  |  | 2.0 |
|   | Cetyl alcohol |  |  | 1.00 | 2.5 |  |
|   | C12-15 Alkyl benzoate |  | 2.5 |  | 4.0 |  |
|   | Dicapryl ether |  | 4.0 |  |  | 6.0 |
|   | Butylene glycol dicaprylate/dicaprate | 4.0 |  | 2.0 | 1.0 |  |
|   | Dicapryl carbonate |  | 2.0 | 3.0 |  | 4.0 |
|   | Cyclopentasiloxane, cyclohexasiloxane |  |  |  | 2.0 | 0.5 |
|   | Prunus Amygdalus Dulcis (Sweet Almond) oil | 2.0 |  | 0.5 |  |  |
|   | Shea butter |  | 2.0 |  | 1.0 |  |
|   | Hydrogenated polyisobutene | 3.0 | 1.0 | 7.0 | 0.5 | 2.0 |
|   | Squalane |  |  |  | 2.0 | 0.5 |
|   | Vitamin E acetate | 0.50 |  | 0.25 |  | 1.00 |
| B | Acrylate/C10-30 alkyl acrylate crosspolymer | 0.3 | 0.1 | 0.2 | 0.15 | 0.2 |
| C | Aqua | ad 100 | ad 100 | ad 100 | ad 100 | ad 100 |
|   | Polyacrylamide, C13-14 isoparaffin, Laureth-7 |  | 1.0 | 1.5 | 0.75 |  |
|   | PUR thickener A.1 | 2.5 | 2.0 | 0.9 | 1.5 | 3.0 |
|   | Propylene Glycol | 3.00 | 5.0 | 2.5 | 7.50 | 10.0 |
| D | Sodium Hydroxide | 0.12 | 0.04 | 0.08 | 0.06 | 0.08 |
| E | Niacinamide | 0.30 | 3.0 | 1.5 | 0.5 | 0.20 |
|   | Aqua | 2.0 | 10.0 | 5.0 | 2.0 | 2.0 |
| F | DMDM Hydantoin |  | 0.60 | 0.45 | 0.25 |  |
|   | Methylparaben |  |  | 0.25 | 0.15 |  |
|   | Phenoxyethanol | 0.50 | 0.40 |  | 1.00 |  |
|   | Ethylhexylglycerin |  |  | 1.00 |  | 0.80 |
|   | Ethanol | 3.00 | 2.00 | 1.50 |  | 7.00 |
| G | Fragrance | 0.20 |  | 0.05 |  | 0.40 |

Preparation:

Heat phases A and C separately to ca. 80° C.

Stir phase B into phase A and then phase C into phase A/B. Briefly homogenize. Add phase D and cool with stirring to ca. 40° C. Add phase E and cool with stirring to ca. 30° C. Add phase F and G to the emulsion and cool to room temperature with stirring. Briefly homogenize.

Instead of the hydrodispersion comprising polyurethane thickener A.1, hydrodispersions comprising one or more of the polyurethanes A.2, A.3, A.4, A.5 or A.6 are also prepared.

Solids-Stabilized Emulsion

| Phase | Ingredients/INCI | F.5.1 | F.5.2 | F.5.3 | F.5.4 | F.5.5 |
|---|---|---|---|---|---|---|
| A | Mineral oil | 4.0 | 6.0 | 16.0 | 10.0 | 6.0 |
|   | Octyldodecanol | 9.0 | 9.0 | 5.0 |  |  |
|   | Ethylhexyl isononanoate | 9.0 | 9.0 | 6.0 | 5.0 | 8.0 |
|   | Isohexadecane | 9.0 | 5.0 |  | 4.0 | 8.0 |
|   | Dimethicone | 0.5 | 2.0 | 1.0 |  | 1.5 |
|   | Cera Microcristallina, Paraffinum Liquidum |  | 0.35 |  | 0.75 | 3.0 |
|   | Phenyl trimethicone | 2.0 |  | 1.0 | 2.5 | 3.0 |
|   | Silica | 2.5 |  |  | 6.0 | 2.5 |
|   | Aluminum starch octenylsuccinate | 2.0 | 1.0 | 0.5 |  |  |
|   | Tapioca starch |  | 0.5 |  |  |  |
| B | Titanium dioxide, coated | 1.0 | 0.5 | 3.0 | 2.0 | 4.0 |
|   | Zinc oxide | 5.0 | 10.0 | 2.0 | 3.0 |  |
| C | Ammonium Acryloyldimethyltaurate/Beheneth-25 Methacrylate Crosspolymer | 0.2 |  | 1.0 | 0.5 |  |

-continued

| Phase | Ingredients/INCI | F.5.1 | F.5.2 | F.5.3 | F.5.4 | F.5.5 |
|---|---|---|---|---|---|---|
| D | Aqua | ad 100 | ad 100 | ad 100 | ad 100 | ad 100 |
|  | Hydroxypropyl Methylcellulose |  |  | 0.1 |  | 0.05 |
|  | Sorbitol | 5.0 | 7.0 | 8.5 | 3.0 | 4.5 |
|  | PUR thickener A.1 | 3.0 | 5.0 | 0.9 | 1.4 | 2.0 |
| E | Mixed parabens | 0.3 | 0.6 | 0.2 |  | 0.4 |
|  | Phenoxyethanol | 0.2 | 0.3 | 0.4 | 0.5 | 0.4 |
|  | Diazolidinyl urea |  |  |  | 0.23 | 0.2 |
| F | Perfume |  | 0.2 | 0.3 |  | 0.1 |

Preparation:

Heat phase A to 80° C.

Add phase B to phase A and homogenize for 3 min. Stir in phase C.

Allow cellulose (if required) to preswell in water, then add the remaining ingredient of phase D and heat to 80° C.

Stir phase D into phase A+B+C and homogenize. Cool emulsion with stirring to ca. 40° C. and add phase E and F. With stirring, cool to RT and homogenize.

Instead of the solids-stabilized emulsion comprising polyurethane thickener A.1, solids-stabilized emulsions comprising one or more of the polyurethanes A.2, A.3, A.4, A.5 or A.6 are also prepared.

Sunscreen Cream

| Phase | Ingredients/INCI | F.6.1 | F.6.2 | F.6.3 | F.6.4 | F.6.5 |
|---|---|---|---|---|---|---|
| A | Aqua | ad 100 | ad 100 | ad 100 | ad 100 | ad 100 |
|  | Disodium EDTA | 0.1 | 0.1 | 0.1 | 0.1 | 0.1 |
|  | Glycerin | 3.00 | 7.50 | 8.0 | 7.50 | 5.00 |
|  | Benzophenone-4 | 2.0 |  |  | 4.0 |  |
|  | Phenylbenzimidazole sulfonic acid |  | 0.50 | 4.00 |  | 8.0 |
|  | Triethanolamine | 1.0 | 0.25 | 2.0 | 2.0 | 4.0 |
|  | Panthenol | 0.5 |  | 0.75 |  | 1.0 |
|  | PUR thickener A.1 | 2.5 g | 0.5 g | 2.0 g | 4.0 | 1.5 |
|  | Xanthan gum |  | 0.3 | 0.15 |  | 0.2 |
| B | Octocrylene | 8.0 |  |  | 7.5 |  |
|  | Ethylhexyl methoxycinnamate, diethylamino hydroxybenzoyl hexyl benzoate | 5.0 | 10.0 | 8.0 | 3.0 | 7.0 |
|  | Steareth-21 | 2.0 | 3.0 |  | 2.5 |  |
|  | Steareth-2 | 1.5 |  |  |  |  |
|  | PEG-40 stearate |  |  | 1.0 |  | 2.0 |
|  | Glycerin monostearate SE |  | 1.0 | 3.0 | 1.5 | 1.5 |
|  | Dibutyl adipate | 3.0 | 5.0 | 3.5 | 2.5 | 2.0 |
|  | Cetearyl alcohol | 2.0 |  |  | 0.5 | 3.0 |
|  | Stearyl alcohol | 1.5 | 3.0 | 2.5 | 0.6 | 2.0 |
|  | Butyrospermum Parkii (Shea Butter) | 1.0 | 0.5 |  | 1.0 | 1.5 |
|  | Dimethicone | 1.0 | 0.5 | 1.5 | 0.8 | 2.0 |
|  | PVP hexadecane copolymer | 0.20 |  | 0.50 | 0.8 | 1.00 |
|  | Bisabolol | 0.2 | 0.1 |  |  | 0.3 |
| C | DMDM hydantoin | 0.5 | 0.5 | 0.5 | 0.5 | 0.75 |
|  | Water, Aloe Barbadensis Leaf Juice |  |  | 0.5 | 1.0 |  |
|  | Alpha-glucosylrutin | 0.60 | 0.5 | 0.4 | 0.25 | 0.3 |
|  | Perfume | 0.10 | 0.25 | 0.30 | 0.40 | 0.20 |

Preparation:

Heat phases A and B separately to ca. 80° C.

Stir phase A into phase B and briefly homogenize.

Cool to ca. 40° C. with stirring. Add components of phase C to the emulsion in succession and cool to room temperature with stirring. Briefly homogenize.

Instead of the sunscreen cream comprising polyurethane thickener A.1, sunscreen creams comprising one or more of the polyurethanes A.2, A.3, A.4, A.5 or A.6 are also prepared.

Face Cream with Sodium Ascorbyl Phosphate

| Phase | Ingredients/INCI | F.7.1 | F.7.2 | F.7.3 | F.7.4 | F.7.5 |
|---|---|---|---|---|---|---|
| A | Water | ad 100 | ad 100 | ad 100 | ad 100 | ad 100 |
|  | Butylene glycol | 5.0 | 6.5 | 5.5 | 3.5 | 4.0 |
|  | PUR thickener A.1 | 3.5 | 1.5 | 2.5 | 5.0 | 2.0 |
|  | Xanthan gum | 0.25 |  | 0.2 | 0.1 |  |
|  | Potassium sorbate | 0.1 | 0.1 | 0.1 | 0.1 | 0.1 |
|  | Imidazolidinyl urea | 0.3 |  | 0.2 |  |  |
| B | Potassium cetyl phosphate | 1.5 | 2.0 | 1.9 | 2.5 | 1.0 |
|  | Caprylic/capric triglyceride | 2.0 | 5.0 | 3.0 | 4.0 | 2.5 |
|  | Stearyl alcohol | 0.5 | 1.5 | 2.0 | 1.0 | 3.0 |
|  | Cetearyl alcohol, dicetyl phosphate, Ceteth-10 phosphate | 1.5 | 2.0 | 1.8 | 1.9 | 2.1 |
|  | Simmondsia Chinensis (Jojoba) seed oil | 3.0 | 1.5 | 0.5 | 1.0 | 2.5 |
|  | Mineral oil | 2.0 | 5.0 | 10.0 | 7.5 | 4.0 |
|  | Paraben mixture | 0.2 | 0.2 | 0.2 | 0.2 | 0.2 |
| C | Sodium ascorbyl phosphate | 5.0 | 2.0 | 3.0 | 4.0 | 1.5 |
|  | Lactic acid | q.s. | q.s. | q.s. | q.s. | q.s. |
|  | Water | 10.0 | 4.0 | 5.0 | 10.0 | 3.0 |
| D | Tocopherol | 0.1 |  |  | 0.2 |  |
|  | Retinol |  | 0.03 | 0.025 |  | 0.05 |
| E | Fragrance | 0.1 | 0.05 | 0.05 | 0.1 | 0.15 |

Preparation

Heat phases A and B separately to 80° C.

Stir phase A into phase B and homogenize.

Stir phase C into phase A+B and homogenize.

Cool to ca. 40° C. with stirring. Adjust pH of phase C to <6.5 with lactic acid. Add phase C and cool to ca. 30° C. with stirring. Add phase D and E. Cool to room temperature with stirring and briefly homogenize.

Note: adjust pH of the emulsion to <6.5 with lactic acid.

Instead of the face cream comprising polyurethane thickener A.1, face creams comprising one or more of the polyurethanes A.2, A.3, A.4, A.5 or A.6 are also prepared.

Hydroxycarboxyclic Acid Cream

| Phase | Ingredients/INCI | F.8.1 | F.8.2 | F.8.3 |
|---|---|---|---|---|
| A | Ceteareth-6, stearyl alcohol | 2.0 |  | 2.5 |
|  | Ceteareth-25 | 2.0 |  | 2.5 |
|  | PEG-100 stearate, glyceryl stearate |  | 3.5 | 0.5 |
|  | Polyglyceryl-3 distearate |  | 2.0 |  |
|  | Mineral oil | 8.0 | 3.5 | 5.0 |
|  | Cetearyl ethylhexanoate | 7.0 | 5.5 | 4.0 |
|  | Sorbitan stearate | 0.5 | 1.5 | 0.5 |
|  | Cera Alba |  | 0.5 | 1.0 |
|  | Cetyl alcohol | 1.5 | 3.5 | 4.0 |
|  | Dimethicone | 0.2 | 2.0 | 0.5 |
| B | Panthenol | 1.0 | 0.5 | 0.3 |
|  | Propylene glycol | 3.0 | 2.0 | 5.0 |
|  | PUR thickener A.1 | 1.0 | 3.0 | 5.0 |
|  | Hydroxy acid | 3.0 | 7.0 | 10.0 |
|  | Aqua | ad 100 | ad 100 | ad 100 |
| C | Sodium hydroxide | q.s. | q.s. | q.s. |
| D | Bisabolol | 0.2 | 0.1 | 0.3 |
|  | Preservative | q.s. | q.s. | q.s. |
|  | Fragrance | q.s. | q.s. | q.s. |

Note

Alpha-hydroxy acids: lactic acid, citric acid, malic acid, glycolic acid

Dihydroxy acid: tartaric acid

Beta-hydroxy acid: salicylic acid

Adjust pH to >3

Preparation

Heat phase A and B separately to ca. 80° C. Adjust pH of phase B to >3 if necessary using NaOH. Stir phase B into phase A, briefly homogenize.

Cool to ca. 40° C. with stirring, add components of phase D in succession, homogenize again.

Instead of the hydroxycarboxylic acid cream comprising polyurethane thickener A.1, hydroxycarboxylic acid creams comprising one or more of the polyurethanes A.2, A.3, A.4, A.5 or A.6 are also prepared.

Emulsion with Deodorant Active Ingredient

| Phase | Ingredients/INCI | F.9.1 | F.9.2 | F.9.3 | F.9.4 | F.9.5 |
|---|---|---|---|---|---|---|
| | Ceteareth-6, stearyl alcohol | 1.5 | 2.0 | | | 1.0 |
| | Ceteareth-25 | 1.5 | 0.5 | | | 1.0 |
| | PEG-40 hydrogenated castor oil | 0.5 | 1.0 | 2.0 | | |
| | Glyceryl stearate | | 0.5 | 2.0 | 1.0 | |
| | Cetyl alcohol | 2.0 | 1.0 | 0.5 | 2.5 | 0.2 |
| | Hydrogenated coco-glycerides | 2.0 | | | 1.0 | 0.5 |
| | Hydrogenated polyisobutene | | 10.0 | 20.0 | 5.0 | 3.0 |
| | Decyl oleate | 3.0 | 2.0 | | 8.0 | 5.0 |
| | Bis-PEG/PPG-14/14 dimethicone, cyclopentasiloxane | 3.0 | 3.5 | 4.0 | 2.0 | 1.5 |
| | Talc | 3.0 | 2.5 | | | 1.5 |
| | Magnesium aluminum silicate | 1.0 | | 0.5 | 1.0 | 1.5 |
| B | Propylene glycol | 10.0 | 5.0 | 7.5 | 20.0 | 15.0 |
| | PUR thickener A.1 | 0.5 | 1.0 | 3.0 | 3.5 | 2.0 |
| | Xanthan gum | 0.2 | 0.1 | | | 0.05 |
| | Cetyl hydroxyethylcellulose | 0.3 | | | 0.1 | |
| | Aluminum chlorohydrate | 5.0 | 10.0 | 20.0 | | |
| | Aluminum zirconium tetrachlorohydrex GLY | | 15.0 | | 50.0 | 20.0 |
| | Aqua | ad 100 | ad 100 | ad 100 | ad 100 | ad 100 |
| C | Neutralizing agent | q.s. | q.s. | q.s. | q.s. | q.s. |
| D | Alcohol | 5.0 | 10.0 | 25.0 | 7.5 | 6.0 |
| | Allantoin | 0.1 | 0.1 | 0.1 | 0.1 | 0.1 |
| | Preservative | q.s. | q.s. | q.s. | q.s. | q.s. |
| | Fragrance | q.s. | q.s. | q.s. | q.s. | q.s. |

Preparation

Heat phases A and B separately to ca. 80° C.

Stir phase B into phase A with homogenization. If appropriate, adjust to pH 4-5 using phase C. Cool to ca. 40° C., add phase D and allow to cool to room temperature with stirring. Briefly homogenize.

Note: adjust pH of the emulsion to 4-5

Instead of the emulsion with deodorant active ingredient comprising polyurethane thickener A.1, emulsions with deodorant active ingredient comprising one or more of the polyurethanes A.2, A.3, A.4, A.5 or A.6 are also prepared.

Hair Removal Cream

| Phase | Ingredients/INCI | F.10.1 | F.10.2 | F.10.3 |
|---|---|---|---|---|
| A | Glyceryl stearate | 1.0 | | |
| | Ceteareth-12 | | 1.0 | 2.0 |
| | Ceteareth-20 | | 1.0 | 2.0 |
| | Stearyl alcohol | | 4.0 | 1.0 |
| | Cetyl alcohol | 4.0 | | 1.0 |
| | Mineral oil | | 6.0 | 4.0 |
| | Prunus Armeniaca (Apricot) kernel oil | 3.0 | 1.0 | 2.0 |
| B | Propylene glycol | 1.0 | 2.0 | 10.0 |
| | Calcium carbonate | 10.0 | | |
| | Calcium hydroxide | 7.0 | | |
| | Sodium hydroxide | | 0.4 | 0.6 |
| | Calcium thioglycolate | 5.0 | 3.0 | 5.0 |
| | PUR thickener A.1 | 3.0 | 1.5 | 2.0 |
| | Aqua | ad 100 | ad 100 | ad 100 |
| C | Tocopherol | 0.1 | 0.2 | 0.15 |
| | Bisabolol | 0.2 | 0.1 | 0.3 |
| | Fragrance | q.s. | q.s. | q.s. |

Preparation

Heat phase A and B separately to ca. 80° C.

Stir phase B into phase A with homogenization, briefly homogenize.

Cool to ca. 40° C., add phase C, cool to RT with stirring and homogenize again.

Note: adjust pH of the emulsion to >10.

Instead of the hair removal cream comprising polyurethane thickener A.1, hair removal creams comprising one or more of the polyurethanes A.2, A.3, A.4, A.5 or A.6 are also prepared.

Self-Tanning Emulsion

| Phase | Ingredients/INCI | F.11.1 | F.11.2 | F.11.3 | F.11.4 |
|---|---|---|---|---|---|
| A | Isohexadecane | 4.0 | 2.0 | 3.0 | 1.0 |
| | Dimethicone | 1.0 | 1.0 | 0.5 | 1.5 |
| | Cetearyl alcohol | 2.0 | 2.5 | 1.5 | 2.5 |
| | Isopropyl myristate | 1.0 | | 2.0 | 3.0 |
| | Simmondsia Chinensis (Jojoba) seed oil | 2.0 | 1.0 | 0.5 | 0.5 |
| | Polyglyceryl-3 methylglucose distearate | 3.0 | | 3.5 | |
| | PEG-40 stearate | | 2.5 | | 2.0 |
| | Lecithin | 0.5 | | | 1.0 |
| | Cetearyl glucoside | 0.5 | | 0.5 | |
| | Sorbitan oleate | | 0.5 | 0.5 | 0.3 |
| B | Glycerin | 4.0 | | | 5.0 |
| | Butylene glycol | | 4.0 | 3.0 | |
| | PUR thickener A.1 | 1.0 | 3.0 | 1.5 | 2.5 |
| | Xanthan gum | 0.1 | | | 0.1 |
| | Aqua | ad 100 | ad 100 | ad 100 | ad 100 |
| C | Dihydroxyacetone | 1.5 | 5.0 | | |
| | Erythrulose | | | 2.0 | 4.0 |
| | Aqua | 5.0 | 10.0 | 5.0 | 8.0 |
| | Citric acid | q.s. | q.s. | q.s. | q.s. |
| D | Bisabolol | 0.3 | 0.5 | 0.2 | 0.4 |
| | Tocopheryl acetate | 0.7 | 0.5 | 0.6 | 1.0 |
| | Preservative | q.s. | q.s. | q.s. | q.s. |
| | Fragrance | q.s. | q.s. | q.s. | q.s. |

Preparation

Heat phases A and B separately to ca. 80° C.

Stir phase B into phase A and briefly homogenize.

With stirring, cool to ca. 40° C., add phase C and cool to 30° C. with stirring. Add components of phase D in succession and cool to RT with stirring. Briefly homogenize.

Note: adjust pH of the emulsion to 4-5.5

Instead of the self-tanning emulsion comprising polyurethane thickener A.1, self-tanning emulsions comprising one or more of the polyurethanes A.2, A.3, A.4, A.5 or A.6 are also prepared.

Conditioner Shampoo

| Ingredients/INCI | F.12.1 | F.12.2 | F.12.3 | F.12.4 |
|---|---|---|---|---|
| Aqua | ad 100 | ad 100 | ad 100 | ad 100 |
| Sodium laureth sulfate | 35.7 | | 30.0 | 12.0 |
| Cocamidopropyl betaine | 13.5 | 15.0 | | |
| Disodium cocoamphodiacetate | | 10.0 | | |
| Sodium cocoamphoacetate | | | 6.0 | |
| Polysorbate 20 | | 5.0 | | |
| Decyl glucoside | | 5.0 | | 1.5 |
| Laureth-3 | | 2.0 | | |
| Sodium laureth sulfate, glycol distearate, cocamide MEA, laureth-10 | | | 3.0 | 2.0 |
| Coco-glucoside, glyceryl oleate | | | | 5.0 |
| Dimethicone | | | 2.0 | |
| Conditioning polymer | 2.0 | 0.5 | 0.75 | 0.4 |
| PUR thickener A.1 | 0.75 | 1.2 | 0.5 | 1.0 |
| PEG-150 distearate | | 3.0 | | |
| Citric acid | | q.s. | q.s. | |
| Preservative | q.s. | q.s. | q.s. | q.s. |
| Fragrance | q.s. | q.s. | q.s. | q.s. |
| Dye | q.s. | q.s. | q.s. | q.s. |
| Sodium chloride | | | 1.0 | 1.0 |

Conditioning polymer is understood as meaning polyquaternium-7, PQ-10, PQ-16, PQ-39, PQ-44, PQ-46, PQ-67, guar hydroxypropyltrimonium chloride, PQ-87, and combinations of these.

Instead of the conditioner shampoo comprising polyurethane thickener A.1, conditioner shampoos comprising one or more of the polyurethanes A.2, A.3, A.4, A.5 or A.6 are also prepared.

Hair Conditioner

| Phase | Ingredients/INCI | F.13.1 | F.13.2 | F.13.3 | F.13.4 | F.13.5 |
|---|---|---|---|---|---|---|
| A | Water | ad 100 | ad 100 | ad 100 | ad 100 | ad 100 |
|   | PUR thickener A.1 | 2.5 | 1.5 | 3.0 | 0.6 | 2.0 |
|   | Hydroxyethylcellulose | 0.05 | 0.1 | | 0.2 | |
|   | Propylene glycol | 1.0 | 2.0 | | 0.8 | 0.5 |
|   | Panthenol | 0.5 | | 0.75 | 0.25 | 0.3 |
| B | Quaternium-91, cetearyl alcohol, cetrimonium methosulfate | 2.0 | | | | 1.5 |
|   | Distearoyethyl hydroxyethylmonium methosulfate, cetearyl alcohol | | | 3.0 | 4.0 | |
|   | Hydrogenated polyisobutene | 1.0 | 1.5 | | 1.0 | |
|   | Cyclopentasiloxane | | | 2.0 | 1.0 | 0.5 |
|   | Isopropyl palmitate | | 1.0 | | 2.0 | |
|   | Persea Gratissima (Avocado) oil | | | | | 2.5 |
|   | Steareth-2 | 0.75 | | 0.5 | | |
|   | Ceteareth-6, stearyl alcohol | | 1.5 | | | 0.5 |
|   | Ceteareth-25 | | 1.5 | | | |
|   | Cetearyl alcohol | 2.0 | 1.5 | 0.5 | 4.0 | |
| C | Acrylate/C10-30 alkylacrylate copolymer | 0.1 | | | 0.2 | 0.15 |
| D | Cetrimonium chloride | 1.5 | | 3.0 | | |
|   | Conditioning polymer | 2.0 | 6.0 | 3.0 | 1.5 | 0.8 |
| E | Preservative | q.s. | q.s. | q.s. | q.s. | q.s. |
|   | Fragrance | q.s. | q.s. | q.s. | q.s. | q.s. |

Conditioning polymer is understood as meaning polyquaternium-7, PQ-10, PQ-16, PQ-39, PQ-44, PQ-46, PQ-67, guar hydroxypropyltrimonium chloride, PQ-87, and combinations of these.

Preparation

Heat phases A and B separately to ca. 80° C.

Stir phase C into phase B, then stir phase A into phase B/C and briefly homogenize.

With stirring, cool to ca. 50° C., add components of phase D in succession and cool to ca. 30° C. with stirring. Add components of phase E in succession and cool to RT with stirring. Briefly homogenize.

Instead of the hair conditioner comprising polyurethane thickener A.1, hair conditioners comprising one or more of the polyurethanes A.2, A.3, A.4, A.5 or A.6 are also prepared.

What is claimed is:

1. A process for preparing polyurethanes comprising
preparing a mixture comprising: at least one polyetherdiol, at least one alkoxylated alcohol, and a catalyst comprising at least one carboxylic acid salt of at least one metal selected from the group consisting of alkali metals, alkaline earth metals, zinc and mixtures thereof, wherein the mixture comprises less than 10 ppm of tin;
providing at least one diisocyanate to the mixture to form a reaction mixture; and
reacting the reaction mixture to form the polyurethanes in a single stage process;
wherein the polyurethanes comprise
I) at least two hydrophilic sections S,
II) at least one hydrophilic section P different from S,
III) at least two terminal hydrophobic sections T,
IV) at least two hydrophobic sections D different from T, and wherein
a) to each section T is directly attached a section S,
b) to each section S on at least one side is attached at least one section D,
c) to each section P are attached at least two sections D.

2. The process according to claim 1, further comprising using a solvent, wherein the solvent is not used to introduce the hydrophilic and hydrophobic sections into the polyurethanes, and the solvent is in the range from 0 to 10% by weight based on the reaction mixture.

3. The process according to claim 1, wherein the at least one hydrophilic section P has a number-average molecular weight of from 4000 to 12 000 g/mol.

4. The process according to claim 1, wherein the carboxylic acid salt comprises potassium carboxylate.

5. The process according to claim 1, wherein the carboxylic acid salt comprises zinc carboxylate.

6. The process according to claim 1, wherein the at least one alkoxylated alcohol comprises at least one
a C4-C30-alcohol ethoxylated with 2 to 100 mol of ethylene oxide per mole, and the polyetherdiol has a molecular weight Mn in the range from 4000 to 12 000 g/mol.

7. The process according to claim 5, wherein the at least one alkoxylated alcohol comprises at least one
C4-C30-alcohol ethoxylated with 2 to 100 mol of ethylene oxide per mole, and the polyetherdiol has a molecular weight Mn in the range from 4000 to 12 000 g/mol.

* * * * *